US010925938B2

(12) United States Patent
Remaley et al.

(10) Patent No.: US 10,925,938 B2
(45) Date of Patent: *Feb. 23, 2021

(54) COMPOSITION COMPRISING PCSK9 PEPTIDE CONJUGATED TO A QBETA CARRIER AND METHODS OF USING THE SAME

(71) Applicants: THE USA, AS REPRESENTED BY THE SECRETARY, DEPT. OF HEALTH AND HUMAN SERVICES, Bethesda, MD (US); UNM Rainforest Innovations, Albuquerque, NM (US)

(72) Inventors: Alan Remaley, Bethesda, MD (US); John T. Schiller, Kensington, MD (US); Marcelo Amar, Gaithersburg, MD (US); Bryce Chackerian, Albuquerque, NM (US)

(73) Assignees: THE USA, AS REPRESENTED BY THE SECRETARY, DEPT. OF HEALTH AND HUMAN SERVICES, Bethesda, MD (US); UNM Rainforest Innovations, Albuquerque, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 16/250,514

(22) Filed: Jan. 17, 2019

(65) Prior Publication Data

US 2019/0134170 A1 May 9, 2019

Related U.S. Application Data

(63) Continuation of application No. 15/118,143, filed as application No. PCT/US2015/015408 on Feb. 11, 2015, now Pat. No. 10,279,019.

(60) Provisional application No. 61/938,450, filed on Feb. 11, 2014.

(51) Int. Cl.
| | |
|---|---|
| *A61K 39/005* | (2006.01) |
| *A61P 9/10* | (2006.01) |
| *C07K 9/00* | (2006.01) |
| *C07K 11/00* | (2006.01) |
| *A61K 39/00* | (2006.01) |
| *A61K 38/10* | (2006.01) |
| *C12N 9/64* | (2006.01) |
| *A61K 47/69* | (2017.01) |
| *A61K 45/06* | (2006.01) |
| *C07K 14/47* | (2006.01) |

(52) U.S. Cl.
CPC .......... *A61K 39/0005* (2013.01); *A61K 38/10* (2013.01); *A61K 45/06* (2013.01); *A61K 47/6901* (2017.08); *A61P 9/10* (2018.01); *C12N 9/6454* (2013.01); *C12Y 304/21061* (2013.01); *A61K 2039/60* (2013.01); *A61K 2039/627* (2013.01); *C07K 9/00* (2013.01); *C07K 11/00* (2013.01); *C07K 14/47* (2013.01); *C12N 2795/18123* (2013.01); *C12N 2795/18134* (2013.01); *C12N 2795/18141* (2013.01)

(58) Field of Classification Search
CPC ........ A61K 39/005; C12N 2795/18123; C07K 9/00
See application file for complete search history.

(56) References Cited

U.S. PATENT DOCUMENTS

| | | | |
|---|---|---|---|
| 3,773,946 | A | 11/1973 | Creger et al. |
| 3,930,024 | A | 12/1975 | Creger |
| 4,287,200 | A | 9/1981 | Kawamatsu et al. |
| 4,613,593 | A | 9/1986 | Yamatsu et al. |
| 4,689,344 | A | 8/1987 | Bar-Tana |
| 4,711,896 | A | 12/1987 | Bar-Tana et al. |
| 4,722,840 | A | 2/1988 | Valenzuela et al. |
| 5,071,651 | A | 12/1991 | Sabara et al. |
| 5,374,426 | A | 12/1994 | Sabara et al. |
| 5,756,344 | A | 5/1998 | Onda et al. |
| 5,756,544 | A | 5/1998 | Bisgaier et al. |
| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,339,068 | B1 | 6/2002 | Krieg et al. |
| 6,506,799 | B1 | 1/2003 | Dasseux |
| 6,949,520 | B1 | 9/2005 | Hartman et al. |
| 2011/0052621 | A1 | 3/2011 | Champion et al. |
| 2017/0189503 | A1 | 7/2017 | Remaley et al. |

FOREIGN PATENT DOCUMENTS

| | | | |
|---|---|---|---|
| EP | 0761231 | A1 | 12/1997 |
| EP | 2450382 | A1 | 9/2012 |
| EP | 3104877 | | 12/2016 |
| WO | WO 1990/003184 | A1 | 4/1990 |
| WO | WO 1990/014837 | A1 | 12/1990 |

(Continued)

OTHER PUBLICATIONS

International Patent Application No. PCT/US2015/015408, filed Sep. 18, 2014; International Search Report/Written Opinion, dated May 4, 2015, 15 pages.

(Continued)

*Primary Examiner* — Zachary C Howard
(74) *Attorney, Agent, or Firm* — Mueting Raasch Group

(57) ABSTRACT

A vaccine construct comprising an antigenic PCSK9 peptide and an immunogenic carrier, and methods of using the same that are effective to lower blood cholesterol levels in a mammal and treat dyslipidemias and related disease states in a mammal without the frequency of administration required by passive immunity strategies.

14 Claims, 17 Drawing Sheets

Specification includes a Sequence Listing.

(56) References Cited

FOREIGN PATENT DOCUMENTS

| WO | WO 1992/11291 A1 | 7/1992 |
|---|---|---|
| WO | WO 1993/011291 A1 | 6/1993 |
| WO | WO 1994/2192 A1 | 9/1994 |
| WO | WO 1995/17210 A1 | 6/1995 |
| WO | WO 1996/002555 A1 | 2/1996 |
| WO | WO 1996/011711 A2 | 4/1996 |
| WO | WO 1996/030523 A2 | 10/1996 |
| WO | WO 1998/015631 A1 | 4/1998 |
| WO | WO 1998/016247 A1 | 4/1998 |
| WO | WO 1998/018810 A1 | 5/1998 |
| WO | WO 1998/030530 A1 | 7/1998 |
| WO | WO 1998/036772 A1 | 8/1998 |
| WO | WO 1998/037919 A1 | 9/1998 |
| WO | WO 1998/040100 A1 | 9/1998 |
| WO | WO 1998/052581 A1 | 11/1998 |
| WO | WO 1998/055495 A2 | 12/1998 |
| WO | WO 1998/057659 A1 | 12/1998 |
| WO | WO 1999/000116 A2 | 1/1999 |
| WO | WO 1999/011241 A1 | 3/1999 |
| WO | WO 1999/044636 A2 | 9/1999 |
| WO | WO 1999/052549 A1 | 10/1999 |
| WO | WO 2000/007621 A2 | 2/2000 |
| WO | WO 2000/019833 A2 | 4/2000 |
| WO | WO 2000/023105 A2 | 4/2000 |
| WO | WO 2000/023955 A1 | 4/2000 |
| WO | WO 2000/032227 A2 | 6/2000 |
| WO | WO 2000/041720 A1 | 7/2000 |
| WO | WO 2000/048630 A1 | 8/2000 |
| WO | WO 2000/056358 A2 | 9/2000 |
| WO | WO 2000/062800 A2 | 10/2000 |
| WO | WO 2001/021152 A1 | 3/2001 |
| WO | WO 2001/021207 A2 | 3/2001 |
| WO | WO 2001/022990 A2 | 4/2001 |
| WO | WO 2001/085208 A2 | 11/2001 |
| WO | WO 2002/005690 A1 | 1/2002 |
| WO | WO 2002/056905 A2 | 7/2002 |
| WO | WO 2003/024480 A2 | 3/2003 |
| WO | WO 2003/024481 A2 | 3/2003 |
| WO | WO 2003/092714 A2 | 11/2003 |
| WO | WO 2004/007538 A2 | 1/2004 |
| WO | WO 2006/134423 A2 | 12/2006 |
| WO | WO 2007/026190 A2 | 3/2007 |
| WO | WO 2010/057242 A2 | 5/2010 |
| WO | WO 2011/027257 A2 | 3/2011 |
| WO | WO 2012/131504 A1 | 10/2012 |
| WO | WO 2013/037889 A2 | 3/2013 |
| WO | WO 2015/123291 A1 | 8/2015 |

OTHER PUBLICATIONS

International Patent Application No. PCT/US2015/015408, filed Sep. 18, 2014, International Preliminary Report on Patentability, dated Aug. 25, 2016, 9 pages.
Altschul et al., "Basic Local Alignment Search Tool," *J. Mol. Biol.*, 1990; 215: 403-410.
Altschul et al., "Gapped BLAST and PSI-BLAST: a new generation of protein database search programs," *Nucleic Acids Res.* 1997; 25(17):3389-3402.
Andreau et al, "Formation of Disulfide Bonds in Synthetic Peptides and Proteins," Methods in Molecular Biology, Peptide Synthesis Protocols, 1994; 35: Ch 7; 91-171.
Atherton and Sheppard "Solid Phase Peptide Synthesis: A Practical Approach" IRL Press at Oxford University Press, 1989; 7 pages.
Ausubel (ed), *Current Protocols in Molecular Biology*, John Wiley and Sons, Inc., 1994; 4 pages.
Ballas et al., "Induction of NK Activity in Murine and Human Cells by CpG Motifs in Oligodeoxynucleotides and Bacterial DNA," *J. Immunol.* 1996; 157:1840-1845.
Bisgaier et al., "A novel compound that elevates high density lipoprotein and activates the peroxisome proliferator activated receptor," 1998; *J. Lipid Res.* 39:17-30.
Bowie et al., "Deciphering the Message in Protein Sequences: Tolerance to Amino Acid Substitutions," *Science*, 1990; 247(4948):1306-1310.
Powell and Newman, Vaccine Design: The Subunit and Adjuvant Approach, Trends in Microbiology, 1996; 4(8):334-335.
Chan et al., "A proprotein convertase subtilisin/kexin type 9 neutralizing antibody reduces serum cholesterol in mice and nonhuman primates," *PNAS*, Jun. 16, 2009; 106(24):9820-9825.
Chu et al., "CpG Oligodeoxynucleotides Act as Adjuvants that Switch on T Helper 1 (Th1) Immunity," *J. Exp. Med.*, The Rockefeller University Press, Nov. 17, 1997; 186(10):1623-1631.
Cowdery et al., "Bacterial DNA induces NK cells to produce IFN-gamma in vivo and increases the toxicity of lipopolysaccharides," *J. Immunol*, 1996; 56:4570-4575.
Cunningham et al., "High-Resolution Epitope Mapping of hGH-Receptor Interactions by Alanine-Scanning Mutagenesis," *Science*, 1989; 244:1081-1085.
Davis et al., "CpG DNA Is a Potent Enhancer of Specific Immunity in Mice Immunized with Recombinant Hepatitis B Surface Antigen," *J. Immunol*, 1998; 160: 870-876.
Duff et al.,"Antibody-mediated disruption of the interaction between PCSK9 and the low-density lipoprotein receptor," *Biochem. J.* 2009; 419:577-584.
Giannis et al., "Peptidomimetics for Receptor Ligands—Discovery, Development, and Medical Perspectives," *Angew. Chem. Int. Ed.*, 1993; 32(9):1244-1267.
Golmohammadi et al., "The crystal structure of bacteriophage Qβ at 3.5 Å resolution," *Structure*, May 15, 1996; 4:543-554.
Gonnet et al, "Exhaustive Matching of the Entire Protein Sequence Database," *Science*, Jun. 5, 1992, 256(5062:1443-1445.
Halpern et al., "Bacterial DNA Induces Murine Interferon-γ Production by Stimulation of Interleukin-12 and Tumor Necrosis Factor-a," *Cell Immunol*, 1996; 167:72-78.
Hunter et al., "Aerosol delivery of Virus-like Particles to the genital tract induces local and systemic antibody responses," *Vaccine*, Jun. 20, 2011; 29(28):4584-5492.
Jiang, et al., "Norwalk Virus Genome Cloning and Characterization," *Science*, 1990; 250(4987):1580-1583.
Kanzler et al., "Therapeutic targeting of innate immunity with Toll-like receptor agonists and antagonists," *Nature Medicine*, May 3, 2007; 13(5):552-559.
Klinman et al., "CpG motifs present in bacteria DNA rapidly induce lymphocytes to secrete interleukin 6, interleukin 12, and interferon gamma," Apr. 1996; *Proc. Natl. Acad. Sci. USA*, 93:2879-2883.
Kozlovska et al., "Recombinant RNA phage qβ capsid particles synthesized and self-assembled in *Escherichia coli*," 1993; *Gene*,137:133-137.
Kozlovska et al., "RNA phage Qβ Coat Protein as a Carrier for Foreign Epitopes," *Intervirology*, Feb. 1996; 39:9-15.
Krieg et al., "CpG motifs in bacterial DNA trigger direct B-cell activation," *Nature*, Apr. 6, 1995; 374:546-549.
Krieg, "Immune effects and mechanisms of action of CpG motifs," *Vaccine*, 2000; 19:618-622.
Krieg and Davis,"Enhancing vaccines with immune stimulatory CpG DNA," 2001; *Curr. Opin. Mol. Ther.* vol. 3(1):15-24.
Kwon et al., "Molecular basis for LDL receptor recognition by PCSK9," *PNAS*, Feb. 12, 2008; 105(6):1820-1825.
Li et al., "Secreted PCSK9 promotes LDL receptor degradation in independently of proteolytic activity," *Biochem. J.*, 2007; 406:203-207.
Lipford et al., "CpG-containing synthetic oligonucleotides promote B and cytotoxic T cell responses to protein antigen: A new class of vaccine adjuvants," *Ear. J. Immunol.*, 1997; 27: 2340-2344.
Maniatis et al., *Molecular Cloning: A Laboratory Manual*, 3$^{rd}$ Addition, Cold Spring Harbor Laboratory Press, Cold Spring Harbor, NY, 2001; 20 pages.
Matsui et al., "The Isolation and Characterization of a Norwalk Virus-specific cDNA," *J. Clin. Invest.*, 1991; 87:1456-1461.
McNutt et al., "Catalytic Activity Is not Required for Secreted PCSK9 to Reduce Low Density Lipoprotein Receptors in HepG2 Cells," *J. Biol. Chem.* 2007; 282(29):20799-20803.

(56) References Cited

OTHER PUBLICATIONS

Messina et al., "Stimulation of in vitro murine lymphocyte proliferation by bacterial DNA," *J. Immunol.*, Sep. 15, 1991; 147(6): pp. 1759-1764.
Moldoveami et al., Cpg DNA, a novel immune enhancer for systemic and mucosal immunization with influenza virus, *Vaccine*, 1988; 16(11/12):1216-1224.
Park et al., "Post-transcriptional Regulation of Low Density Lipoprotein Receptor Protein by Proprotein Convertase Subtilisin/Kexin Type 9a in Mouse Liver," *J. Biol. Chem.*, 2004; 279(48): pp. 50630-50638.
Pearson, "Rapid and Sensitive Sequence Comparison with FASTP and FASTA," *Methods Enzymol.*, 1990; 183:63-98.
Pearson, "Using the FASTA Program to Search Protein and DNA Sequence Databases" *Methods Mol. Biol.*, 1994; 24:307-331.
Pearson, "Flexible Sequence Similarity Searching with the FASTA3 Program Package," *Methods Mol. Biol.*, 2000; 132:85-219.
Remington, *The Science and Practice of Pharmacy*, 19th Edition, Mack Publishing Company, 1995, vol. 1, 10 pages.
Roman et al., "Immunostimulatory DNA sequences function as T helper-1-promoting adjuvants," *Nat. Med.*, Aug. 1997; 3(8):849-854.
Roth et al., "Atorvastatin with or without an Antibody to PCSK9 in Primary Hypercholesterolemia," *N. Engl. J. Med.*, 2012; 367(20):1891-1900.
Sasnauskas et al., "Yeast Cells Allow High-Level Expression and Formation of Polyomavirus-Like Particles," *Biol. Chem.*, 1999; 380 (3):381-386.
Sasnauskas et al, 2001 Generation of recombinant virus-like particles of different polyomaviruses in yeast. 3rd International Workshop "Virus-like particles as vaccines." *Intervirology*, 2001; 45:(4/6), 12 pages.
Seidah et al., "The secretory proprotein convertase neural apoptosis-regulated convertase 1 (NARC-1): Liver regeneration and neuronal differentiation," *PNAS*, Feb. 4, 2003; 100(3):928-933.
Sjolander et al., "ISCOMs: an adjuvant with multiple functions," *J. Leukocyte Biol.*, Dec. 1998; 64:713-723.
Smiley et al., "Enhanced readthrough of opal (UGA) stop codons and production of *Mycoplasma pneumoniae* P1 epitopes in *Escherichia coli*," *Gene*, 1993; 134:33-40.
Stacey et al., "Macrophages ingest and are activated by bacterial DNA," *J. Immunol.* 1996; 157:2116-2122.
Twomey et al., "Structure and immunogenicity of experimental foot-and-mouth disease and poliomyelitis vaccines," *Vaccine*, 1995; 13(16):1603-1610.
Tugyi et al., "Partial D-amino acid substitution: Improved enzymatic stability and preserved Ab recognition of a MUC2 epitope peptide" PNAS, Jan. 11, 2005; 102(2):413-8.
Ulrich et al., "Core Particles of Hepatitis B Virus as Carrier for Foreign Epitopes," *Advances in Virus Research*, 1998; 50:141-182.
Warnes et al., "Expression of the measles virus nucleoprotein gene in *Escherichia coli* and assembly of nucleocapsid-like structures," *Gene*, 1995; 160:173-178.
Weiner et al., "Immunostimulatory oligodeoxynucleotides containing the CpG motif are effective as immune adjuvants in tumor antigen immunization," *PNAS USA* Sep. 1997; 94:10833-10837.
Yamamoto et al., "In vitro Augmentation of Natural Killer Cell Activity and Production of Interferon-a/β and -γ with Deoxyribonucleic Acid Fraction from *Mycobacterium bovis* BCG," *Jpn. J. Cancer Res.*, Jul. 1988; vol. 79:866-873.
Yamamoto et al., "Unique palindromic sequences in synthetic oligonucleotides are required to induce INF and augment INF-mediated natural killer activity," *J. Immunol.* 1992; 148:4072-4076.
Yi et al.,"CgG DNA rescue of murine B lymphoma cells from anti-IgM-induced growth arrest and programmed cell death is associated with increased expression of c-myc and bcl-xL," *J. Immunol*, 1996; 157:4918-4925.
Yi et al., "Rapid immune activation by CpG motifs in bacterial DNA. Systemic induction of IL-6 transcription through an antioxidant-sensitive pathway," *J. Immunol*, 1996; 157:5394-5402.
Yi et al., "CpG Motifs in Bacterial DNA Activate Leukocytes Through the pH-Dependent Generation of Reactive Oxygen Species," *J. Immunol*, 1998; 160: 4755-4761.
Yi et al., "CpG Oligodeoxyribonucleotides Rescue Mature Spleen B Cells from Spontaneous Apoptosis and Promote Cell Cycle Entry," *J. Immunol*, 1998; 160: pp. 5898-5906.
Yuan et al., "Subtype-Independent Immature Secretion and Subtype-Dependent Republication Deficiency of a Highly Frequent, Naturally Occurring Mutation of Human Hepatitis B Virus Core Antigen," *J. Virol.*, 1999; 73(12):10122-10128.
Zhang et al., "Binding of Proprotein Convertase Subtilisin/Kexin Type 9 to Epidermal Growth Factor-Like Repeat A of Low Density Lipoprotein Receptor Decreases Receptor Recycling and Increases Degradation," *J. Biol. Chem.*, 2007; 282(25):18602-18612.

SEQUENCE LISTING

<160> NUMBER OF SEQ ID NOS: 5

<210> SEQ ID NO 1
<211> LENGTH: 694
<212> TYPE: PRT
<213> ORGANISM: Mus musculus

<400> SEQUENCE: 1

```
Met Gly Thr His Cys Ser Ala Trp Leu Arg Trp Pro Leu Pro Leu
1               5                   10                  15

Leu Pro Pro Leu Leu Leu Leu Leu Leu Leu Cys Pro Thr Gly Ala
                20                  25                  30

Gly Ala Gln Asp Glu Asp Gly Asp Tyr Glu Glu Leu Met Leu Ala Leu
                35                  40                  45

Pro Ser Gln Glu Asp Gly Leu Ala Asp Glu Ala Ala His Val Ala Thr
            50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Gly Tyr Val Ile
            100                 105                 110

Lys Val Leu His Ile Phe Tyr Asp Leu Phe Pro Gly Phe Leu Val Lys
                115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Asp Arg Ser
                165                 170                 175

Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
    195                 200                 205

Asn Ser Val Pro Glu Glu Asp Gly Thr Arg Phe His Arg Gln Ala Ser
210                 215                 220

Lys Cys Asp Ser His Gly Thr His Leu Ala Gly Val Val Ser Gly Arg
225                 230                 235                 240

Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
            260                 265                 270

Phe Ile Arg Lys Ser Gln Leu Ile Gln Pro Ser Gly Pro Leu Val Val
        275                 280                 285

Leu Leu Pro Leu Ala Gly Gly Tyr Ser Arg Ile Leu Asn Ala Ala Cys
    290                 295                 300

Arg His Leu Ala Arg Thr Gly Val Val Leu Val Ala Ala Gly Asn
305                 310                 315                 320

Phe Arg Asp Asp Ala Cys Leu Tyr Ser Pro Ala Ser Ala Pro Glu Val
                325                 330                 335

Ile Thr Val Gly Ala Thr Asn Ala Gln Asp Gln Pro Val Thr Leu Gly
```

-continued

```
                340                 345                 350
Thr Leu Gly Thr Asn Phe Gly Arg Cys Val Asp Leu Phe Ala Pro Gly
            355                 360                 365
Lys Asp Ile Ile Gly Ala Ser Ser Asp Cys Ser Thr Cys Phe Met Ser
370                 375                 380
Gln Ser Gly Thr Ser Gln Ala Ala His Val Ala Gly Ile Val Ala
385                 390                 395                 400
Arg Met Leu Ser Arg Glu Pro Thr Leu Thr Leu Ala Glu Leu Arg Gln
                405                 410                 415
Arg Leu Ile His Phe Ser Thr Lys Asp Val Ile Asn Met Ala Trp Phe
            420                 425                 430
Pro Glu Asp Gln Gln Val Leu Thr Pro Asn Leu Val Ala Thr Leu Pro
        435                 440                 445
Pro Ser Thr His Glu Thr Gly Gly Gln Leu Leu Cys Arg Thr Val Trp
    450                 455                 460
Ser Ala His Ser Gly Pro Thr Arg Thr Ala Thr Ala Thr Ala Arg Cys
465                 470                 475                 480
Ala Pro Glu Glu Glu Leu Leu Ser Cys Ser Ser Phe Ser Arg Ser Gly
                485                 490                 495
Arg Arg Arg Gly Asp Trp Ile Glu Ala Ile Gly Gln Gln Val Cys
            500                 505                 510
Lys Ala Leu Asn Ala Phe Gly Gly Glu Gly Val Tyr Ala Val Ala Arg
        515                 520                 525
Cys Cys Leu Val Pro Arg Ala Asn Cys Ser Ile His Asn Thr Pro Ala
    530                 535                 540
Ala Arg Ala Gly Leu Glu Thr His Val His Cys His Gln Lys Asp His
545                 550                 555                 560
Val Leu Thr Gly Cys Ser Phe His Trp Glu Val Glu Asp Leu Ser Val
                565                 570                 575
Arg Arg Gln Pro Ala Leu Arg Ser Arg Gln Pro Gly Gln Cys Val
            580                 585                 590
Gly His Gln Ala Ala Ser Val Tyr Ala Ser Cys Cys His Ala Pro Gly
        595                 600                 605
Leu Glu Cys Lys Ile Lys Glu His Gly Ile Ser Gly Pro Ser Glu Gln
    610                 615                 620
Val Thr Val Ala Cys Glu Ala Gly Trp Thr Leu Thr Gly Cys Asn Val
625                 630                 635                 640
Leu Pro Gly Ala Ser Leu Thr Leu Gly Ala Tyr Ser Val Asp Asn Leu
                645                 650                 655
Cys Val Ala Arg Val His Asp Thr Ala Arg Ala Asp Arg Thr Ser Gly
            660                 665                 670
Glu Ala Thr Val Ala Ala Ile Cys Cys Arg Ser Arg Pro Ser Ala
        675                 680                 685
Lys Ala Ser Trp Val Gln
    690

<210> SEQ ID NO 2
<211> LENGTH: 692
<212> TYPE: PRT
<213> ORGANISM: Homo sapiens

<400> SEQUENCE: 2

Met Gly Thr Val Ser Ser Arg Arg Ser Trp Trp Pro Leu Pro Leu Leu
1               5                   10                  15
```

```
Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
```

-continued

```
            435                 440                 445
His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 3
<211> LENGTH: 17
<212> TYPE: PRT
<213> ORGANISM: Homo sapiens

<400> SEQUENCE: 3

Asn Val Pro Glu Glu Asp Gly Thr Arg Phe His Arg Gln Ala Ser Lys
1               5                   10                  15

Cys

<210> SEQ ID NO 4
<211> LENGTH: 17
<212> TYPE: PRT
<213> ORGANISM: Homo sapiens

<400> SEQUENCE: 4

Cys Lys Ser Ala Gln Arg His Phe Arg Thr Gly Asp Glu Glu Pro Val
1               5                   10                  15

Asn

<210> SEQ ID NO 5
<211> LENGTH: 17
```

```
-continued

<212> TYPE: PRT
<213> ORGANISM: Mus musculus

<400> SEQUENCE: 5

Ser Val Pro Glu Glu Asp Gly Thr Arg Phe His Arg Gln Ala Ser Lys
1               5                   10                  15
Cys
```

COMPOSITION COMPRISING PCSK9 PEPTIDE CONJUGATED TO A QBETA CARRIER AND METHODS OF USING THE SAME

This application is a continuation application of U.S. application Ser. No. 15/118,143 filed Aug. 11, 2016, which is the § 371 U.S. National Stage of International Application No. PCT/US2015/015408, filed Feb. 11, 2015, which claims the benefit of U.S. Provisional Application No. 61/938,450, filed Feb. 11, 2014, each of which is incorporated by reference herein in its entirety.

TECHNICAL FIELD

The present invention is related to the fields of molecular biology, virology, immunology and medicine. The invention provides a composition comprising a virus-like particle (VLP) of an RNA-bacteriophage and at least one antigenic PCSK9 peptide, wherein the VLP and the at least one antigen are linked with one another. The invention also provides methods for producing the compositions of the invention. The compositions of the invention are useful in the production of vaccines for the prevention, treatment or alleviation of PCSK9-related disorders, cardiovascular diseases, and other diseases and conditions, including dyslipidemias.

BACKGROUND OF INVENTION

Proprotein convertase subtilisin-kexin type 9 (hereinafter "PCSK9"), is a proteinase K-like subtilase identified as the 9th member of the mammalian PCSK family (Seidah et al, 2003 PNAS 100:928-933). The gene for PCSK9 localizes to human chromosome 1p33-p34.3, and is expressed in cells capable of proliferation and differentiation including, for example, hepatocytes, kidney mesenchymal cells, intestinal ileum, and colon epithelia as well as embryonic brain telencephalon neurons.

Structurally, PCSK9 consists of a 30 amino acid signal peptide, followed by a prodomain (amino acids 31-152), a catalytic domain (amino acids 153-425) and a CHRD (C-terminal cysteine/histidine-rich domain) (amino acids 426-692). PCSK9 is synthesized as an approximately 72 kDa precursor protein that undergoes autocatalytic cleavage in the endoplasmic reticulum. After cleavage, the approximately 14 kDa prodomain remains tightly associated with the active site, rendering the mature protein catalytically inactive. PCSK9 undergoes a variety of post-translational modifications before being secreted efficiently from the cell.

In cell-culture systems, overexpression of PCSK9 resulted in a decrease in LDL-receptor (LDLR) levels via a post-transcriptional mechanism (Park, et al, 2004 J. Biol. Chem. 279:50630-638). It has been shown that PCSK9 forms a direct protein-protein interaction with the EGF-A (epidermal growth factor-like repeat A) domain of the LDLR that results in targeting of the LDLR to lysosomes for degradation (Kwon et al, 2008 PNAS 105:1820-1825; Zhang, et al, 2007 J. Biol. Chem. 282:18602-18612). This interaction appears to be necessary for PCSK9-mediated LDLR degradation (Li et al, 2007 Biochem. J. 406:203-207; McNutt et al, 2007 J. Biol. Chem. 282:20799-20803). Studies using surface plasmon resonance demonstrated that direct binding of PCSK9 to the LDLR could be abolished with three different anti-PCSK9 antibodies, and these antibodies blocked the PCSK9-LDLR interaction by inhibiting the action of PCSK9 produced endogenously (Duff et al, 2009 Biochem. J. 419:577-584). A neutralizing anti-PCSK9 monoclonal antibody that binds an epitope on PCSK9 adjacent to the region required for LDLR interaction was shown to inhibit PCSK9 binding to the LDLR and attenuate PCSK9-mediated reduction in LDLR protein levels, thereby increasing LDL uptake. Additionally, a combination of this antibody with a statin increased LDLR levels in HepG2 cells more than either treatment alone (Chan et al, 2009 PNAS 106:9820-25). Subsequently, a fully human PCSK9 monoclonal antibody was shown to increase the recycling of LDL receptors and reduce LDL cholesterol levels (Roth et al, N Engl J Med 2012, 367:1891-900). Unfortunately, treatment to reduce LDL cholesterol by the administration of anti-PCSK9 antibodies is expensive and requires frequent administration of the antibodies to produce therapeutic effects.

Accordingly, it would be of great therapeutic benefit to produce a vaccine that could safely induce antibodies that antagonize the activity of PCSK9 for the treatment of various therapeutic conditions associated with PCSK9, such as increased plasma levels of LDL cholesterol.

SUMMARY OF INVENTION

The present invention relates to a vaccine construct comprising an antigenic PCSK9 peptide and an immunogenic carrier, as well as methods for producing such vaccine construct, and pharmaceutical compositions comprising such vaccine constructs, as well as uses of such compositions, in the treatment, alleviation or prophylaxis of PCSK9-related disorders. Such pharmaceutical compositions optionally comprise one or several adjuvants. Such pharmaceutical compositions optionally comprise one or several pharmaceutical carriers.

In particular, the invention relates to an antigenic PCSK9 peptide of the invention, or an immunogenic or pharmaceutical composition thereof, for use as a medicament preferably in treatment, alleviation or prophylaxis of diseases associated with elevated levels of cholesterol in a mammal.

The vaccine constructs of the invention are useful in the treatment of patients having, or at risk for, elevated LDL-cholesterol or a condition associated with elevated LDL-cholesterol, e.g., a lipid disorder (e.g., hyperlipidemia, type I, type II, type III, type IV, or type V hyperlipidemia, secondary hypertriglyceridemia, hypercholesterolemia, familial hypercholesterolemia, xanthomatosis, cholesterol acetyltransferase deficiency). The vaccine constructs of the invention are also useful in the treatment of patients having arteriosclerotic conditions (e.g., atherosclerosis), coronary artery disease, cardiovascular disease, and patients at risk for these disorders, e.g., due to the presence of one or more risk factors, such as hypertension, cigarette smoking, diabetes, obesity, or hyperhomocysteinemia. The vaccine constructs of the invention are also useful in the treatment of Alzheimer's disease in a patient.

In certain embodiments, the vaccine constructs of the invention may be administered together with another agent, such as, for example a statin.

The vaccine constructs of the invention comprise a virus-like particle (VLP) comprising coat proteins, mutants or fragments thereof, of an RNA-bacteriophage with at least one first attachment site, and at least one PCSK9 antigen with at least one second attachment site, wherein the at least one PCSK9 antigen and the VLP are linked through the at least one first attachment site and the at least one second attachment site.

One aspect of the invention is an immunogen comprising an antigenic PCSK9 peptide consisting of the amino acid sequence NVPEEDGTRFHRQASKC (SEQ ID NO:3) linked to a bacteriophage Qbeta immunogenic carrier.

Another aspect of the invention is an immunogen comprising an antigenic PCSK9 peptide consisting of the amino acid sequence CKSAQRHFRTGDEEPVN (SEQ ID NO:4) linked to a bacteriophage Qbeta immunogenic carrier.

In these embodiments, at least one of the amino acids may exist in the D-isomeric form.

In this aspect, the immunogenic carrier may be linked to the PCSK9 peptide through a succinimidyl-6-[β-maleimidopropionamido]hexanoate (SMPH) cross-linker molecule.

A related embodiment is a composition comprising the immunogen of this aspect of the invention. Such composition may further comprise at least one adjuvant.

Another related embodiment is a nucleic acid encoding the immunogen of this aspect of the invention, as well as an expression vector comprising such nucleic acid, and a host cell comprising such expression vector.

Another aspect of the invention is a method of preventing, alleviating, or treating a dyslipidemia in an individual, comprising administering a therapeutically effective amount of the immunogen to the individual. Dyslipidemia may include lipid disorders such as hyperlipidemia from type I, type II, type III, type IV, or type V hyperlipidemia, secondary hypertriglyceridemia, secondary hypercholesterolemia, familial hypercholesterolemia, familial combined hyperlipidemia, xanthomatosis, and lecithin:cholesterol acetyltransferase deficiency.

Another aspect of the invention is a method of preventing, alleviating, or treating a condition selected from atherosclerosis, coronary artery disease, cardiovascular disease, and Alzheimer's disease in an individual, comprising administering a therapeutically effective amount of the immunogen to the individual.

This Summary of the Invention is neither intended nor should it be construed as being representative of the full extent and scope of the present invention. Moreover, references made herein to "the present invention," or aspects thereof, should be understood to mean certain embodiments of the present invention and should not necessarily be construed as limiting all embodiments to a particular description. The present invention is set forth in various levels of detail in the Summary of the Invention as well as in the attached drawings and the Description of Embodiments and no limitation as to the scope of the present invention is intended by either the inclusion or non-inclusion of elements, components, etc. in this Summary of the Invention. Additional aspects of the present invention will become more readily apparent from the Description of Embodiments, particularly when taken together with the drawings.

BRIEF DESCRIPTION OF DRAWINGS

FIG. 2A shows that the mice developed a high-titer anti-peptide IgG response that cross-reacted with PCSK9 peptide, and FIG. 2B shows that this anti-peptide IgG also cross-reacted with intact protein.

FIG. 3A shows the serum taken from mice prior to vaccination (prebleed) or after 3 immunizations and then assessed for PCSK9 by ELISA. FIG. 3B shows sera reacted with Protein G (to deplete IgG) and then retested by ELISA for PCSK9.

DESCRIPTION OF ILLUSTRATIVE EMBODIMENTS

Figure 1:
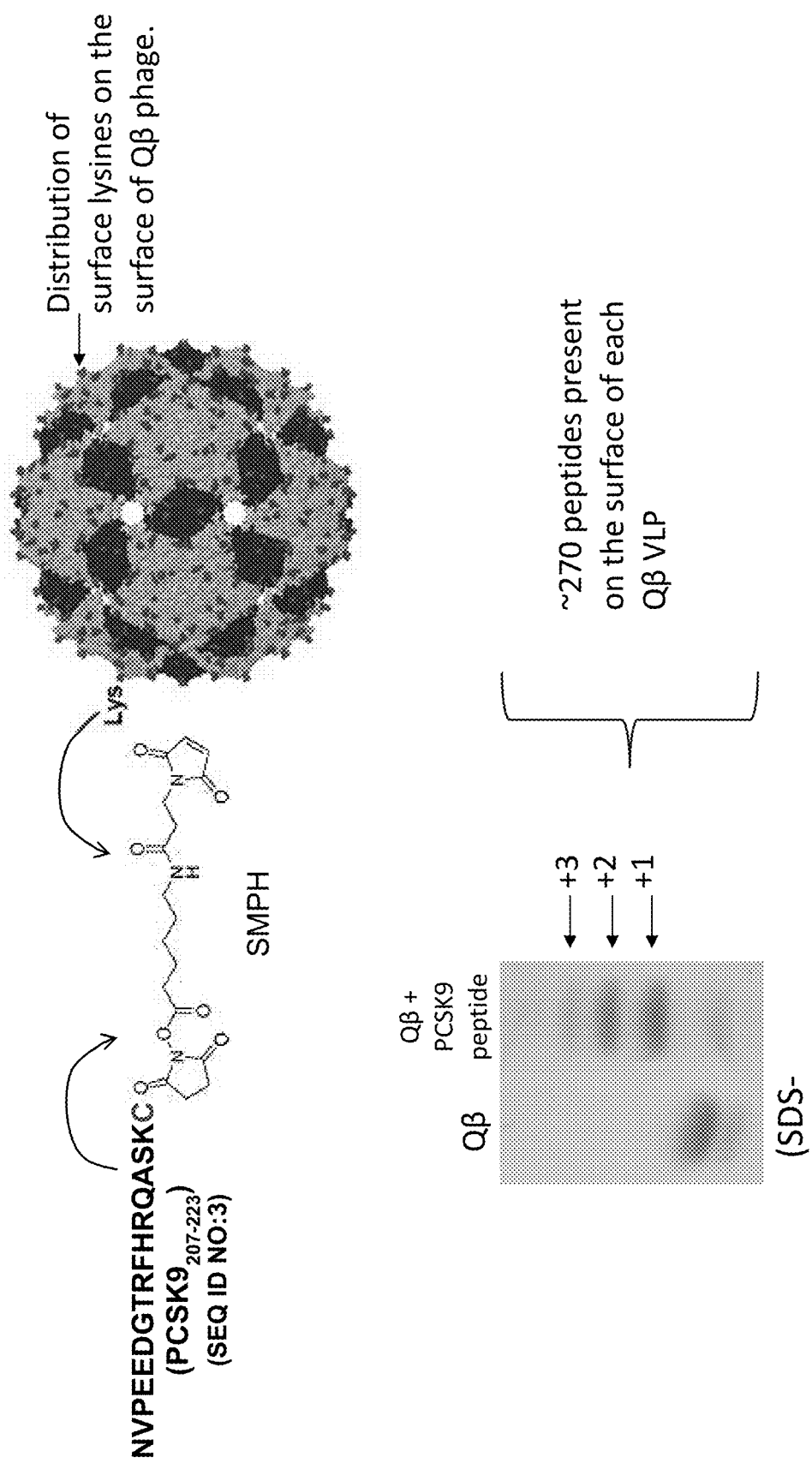
FIG. 1 shows a PCSK9 peptide (SEQ ID NO:3) conjugation to Qbeta bacteriophage VLPs using a bifunctional cross-linker.

The present invention is drawn to a vaccine construct comprising an antigenic PCSK9 peptide and an immunogenic carrier, and methods of using the same that are effective to lower blood cholesterol levels in a mammal and treat dyslipidemias and related disease states in a mammal without the frequency of administration required by passive immunity strategies.

Antigenic PCSK9 Peptide of the Invention

The present invention relates to an immunogen comprising an antigenic PCSK9 peptide linked to an immunogenic carrier.

In one embodiment, the antigenic PCSK9 peptide is a portion of PCSK9 comprising between 4 to 20 amino acids and, when administered to a subject, is able to lower the LDL-cholesterol level in blood of the subject. Preferably, the subject is a mammal, preferably a human. Preferably, the antigenic PCSK9 peptide is able to lower the LDL-cholesterol level by at least 2%, 5%, 10%, 20%, 30%, 50%, or more. In one embodiment, the antigenic PCSK9 peptide is a portion of PCSK9, which participates in the interaction of PCSK9 with the LDL receptor.

In one embodiment, the antigenic PCSK9 peptide is a peptide comprising 5 to 20 consecutive amino acids of the PCSK9 fragment of SEQ ID NO:1 or SEQ ID NO:2. In a specific embodiment, the antigenic PCSK9 peptide is the peptide: NVPEEDGTRFHRQASKC (SEQ ID NO:3). In a specific embodiment, the antigenic PCSK9 peptide is the peptide: CKSAQRHFRTGDEEPVN (SEQ ID NO:4). The antigenic PCSK9 peptide: SVPEEDGTRFHRQASKC (SEQ ID NO:5) is the mouse counterpart to the human fragment of SEQ ID NO:3.

| Sequence Identifier | Sequence |
|---|---|
| Mouse PCSK9 SEQ ID NO: 1 | MGTHCSAWLRWPLLPLLPPLLLLLLLLCPTGAGAQDEDGDYEELMLALPS QEDGLADEAAHVATATFRRCSKEAWRLPGTYIVVLMEETQRLQIEQTAHR LQTRAARRGYVIKVLHIFYDLFPGFLVKMSSDLLGLALKLPHVEYIEEDSF VFAQSIPWNLERIIPAWHQTEEDRSPDGSSQVEVYLLDTSIQGAHREIEGRV TITDFNSVPEEDGTRFHRQASKCDSHGTHLAGVVSGRDAGVAKGTSLHSL RVLNCQGKGTVSGTLIGLEFIRKSQLIQPSGPLVVLLPLAGGYSRILNAACR HLARTGVVLVAAAGNFRDDACLYSPASAPEVITVGATNAQDQPVTLGTL GTNFGRCVDLFAPGKDIIGASSDCSTCFMSQSGTSQAAAHVAGIVARMLSR EPTLTLAELRQRLIHFSTKDVINMAWFPEDQQVLTPNLVATLPPSTHETGG QLLCRTVWSAHSGPTRTATATARCAPEEELLSCSSFSRSGRRRGDWIEAIG GQQVCKALNAFGGEGVYAVARCCLVPRANCSIHNTPAARAGLETHVHCH QKDHVLTGCSFHWEVEDLSVRRQPALRSRRQPGQCVGHQAASVYASCCH APGLECKIKEHGISGPSEQVTVACEAGWTLTGCNVLPGASLTLGAYSVDN LCVARVHDTARADRTSGEATVAAAICCRSRPSAKASWVQ |
| Human PCSK9 SEQ ID NO: 2 | MGTVSSRRSWWPLPLLLLLLLLLGPAGARAQEDEDGDYEELVLALRSEED GLAEAPEHGTTATFHRCAKDPWRLPGTYVVVLKEETHLSQSERTARRLQA QAARRGYLTKILHVFHGLLPGFLVKMSGDLLELALKLPHVDYIEEDSSVFA QSIPWNLERITPPRYRADEYQPPDGGSLVEVYLLDTSIQSDHREIEGRVMVT DFENVPEEDGTRFHRQASKCDSHGTHLAGVVSGRDAGVAKGASMRSLRV LNCQGKGTVSGTLIGLEFIRKSQLVQPVGPLVVLLPLAGGYSRVLNAACQR LARAGVVLVTAAGNFRDDACLYSPASAPEVITVGATNAQDQPVTLGTLGT NFGRCVDLFAPGEDIIGASSDCSTCFVSQSGTSQAAAHVAGIAAMMLSAEP ELTLAELRQRLIHFSAKDVINEAWFPEDQRVLTPNLVAALPPSTHGAGWQ LFCRTVWSAHSGPTRMATAVARCAPDEELLSCSSFSRSGKRRGERMEAQG GKLVCRAHNAFGGEGVYAIARCCLLPQANCSVHTAPPAEASMGTRVHCH QQGHVLTGCSSHWEVEDLGTHKPPVLRPRGQPNQCVGHREASIHASCCH APGLECKVKEHGIPAPQEQVTVACEEGWTLTGCSALPGTSHVLGAYAVD NTCVVRSRDVSTTGSTSEGAVTAVAICCRSRHLAQASQELQ |
| Human PCSK9 antigenic fragment SEQ ID NO: 3 | NVPEEDGTRFHRQASKC |
| Reverse of SEQ ID NO: 3 antigenic fragment SEQ ID NO: 4 | CKSAQRHFRTGDEEPVN |
| Mouse PCSK9 fragment SEQ ID NO: 5 | SVPEEDGTRFHRQASKC |

Such antigenic PCSK9 peptides may be used alone or in combination, preferably when conjugated to an immunogenic carrier, to induce auto anti-PCSK9 antibodies in a subject in order to treat, prevent or ameliorate PCSK9-related disorders. The ability of the antigenic PCSK9 peptides of the invention to induce auto anti-PCSK9 antibodies may be measured in mice, using the test disclosed in Example 1 of the present application. The ability of auto-antibodies induced by the antigenic PCSK9 peptide of the invention to decrease the level of circulating plasma cholesterol may be measured in mice, using the test disclosed in Example 2. The ability of auto-antibodies induced by the antigenic PCSK9 peptide of the invention to inhibit the interaction between PCSK9 and LDL receptors may be measured directly using the FRET assay, or indirectly by measuring the upregulation of cell surface LDL receptors as a consequence of blocking PCSK9-mediated down-regulation (as well described in the relevant literature, either using cell lines in vitro or by measuring LDL receptor levels in liver biopsies of antibody expressing animals (e.g. by Western blotting)).

The term "antigenic PCSK9 peptide biological activity", when used herein, refers to the ability of the antigenic PCSK9 peptides of the invention to induce auto anti-PCSK9 antibodies in a patient.

Vaccine constructs of the invention, when administered to a subject, are able to lower the LDL-cholesterol level in blood of the subject. Preferably, the subject is a mammal, preferably a human. Preferably, the vaccine construct is able to lower the LDL-cholesterol level by at least 2%, 5%, 10%, 20%, 30%, 50%, or more.

The antigenic PCSK9 peptides of the invention include an amino acid sequence derived from a portion of a mammalian PCSK9, preferably a mouse PCSK9 (SEQ ID NO:1) or human PCSK9 (SEQ ID NO:2), such derived portion of PCSK9 either corresponding to the amino acid sequence of naturally occurring PCSK9 or corresponding to variant PCSK9, i.e. the amino acid sequence of naturally occurring PCSK9 in which a small number of amino acids have been substituted, added or deleted but which retains essentially the same immunological properties. In addition, such derived PCSK9 portion can be further modified by amino acids, especially at the N- and C-terminal ends to allow the antigenic PCSK9 peptide to be conformationally-constrained and/or to allow coupling of the antigenic PCSK9 peptide to an immunogenic carrier after appropriate chemistry has been carried out.

In another embodiment, the antigenic PCSK9 peptides of the present invention comprise amino acid variants derived from a portion of a mammalian PCSK9 made with D-amino acids in the order as found in nature, with respect to the N and C-terminus. Thus, in one embodiment, the PCSK9 peptide of the vaccine constructs of the invention comprise an amino acid sequence derived from a portion of a mammalian PCSK9, preferably a mouse PCSK9 (SEQ ID NO:1) or human PCSK9 (SEQ ID NO:2), in which at least one amino acid is in the D-isomeric form. In a related embodiment, the PCSK9 peptide of the vaccine constructs of the invention comprise an amino acid sequence derived from a portion of a mammalian PCSK9, preferably SEQ ID NO:1 or SEQ ID NO:2, in which at all amino acids are in the D-isomeric form. In another embodiment, the PCSK9 peptide of the vaccine constructs of the invention comprise an amino acid sequence derived from a portion of a mammalian PCSK9, preferably SEQ ID NO:1 or SEQ ID NO:2, in which all amino acids are in the D-isomeric form, with the exception of at least one of the N-terminal and C-terminal amino acids, which are in the L-isomeric form. In a specific embodiment, the PCSK9 peptide of the vaccine constructs of the invention comprise an amino acid sequence derived from a portion of a mammalian PCSK9, preferably SEQ ID NO:1 or SEQ ID NO:2, in which all amino acids are in the D-isomeric form, with the exception of the N-terminal and C-terminal amino acids, which are in the L-isomeric form.

In certain embodiments, the PCSK9 peptide of the vaccine constructs of the invention comprise the amino acid sequence NVPEEDGTRFHRQASKC (SEQ ID NO:3), in which at least one amino acid is in the D-isomeric form. In a related embodiment, the PCSK9 peptide of the vaccine constructs of the invention comprise the amino acid sequence NVPEEDGTRFHRQASKC (SEQ ID NO:3), in which at all amino acids are in the D-isomeric form. In another embodiment, the PCSK9 peptide of the constructs of the invention comprise the amino acid sequence NVPEEDGTRFHRQASKC (SEQ ID NO:3), in which all amino acids are in the D-isomeric form, with the exception of at least one of the N-terminal and C-terminal amino acids, which are in the L-isomeric form. In a specific embodiment, the PCSK9 peptide of the vaccine constructs of the invention comprise the amino acid sequence NVPEEDGTRFHRQASKC (SEQ ID NO:3), in which all amino acids are in the D-isomeric form, with the exception of both the N-terminal and C-terminal amino acids, which are in the L-isomeric form.

In another embodiment, the antigenic PCSK9 peptides of the present invention comprise amino acid variants derived from a portion of a mammalian PCSK9 made with D-amino acids in the reverse order with respect to the N and C-terminus. Thus, in one embodiment the PCSK9 peptide of the vaccine constructs of the invention comprise an amino acid sequence derived from a portion of a mammalian PCSK9, preferably a mouse PCSK9 (SEQ ID NO:1) or human PCSK9 (SEQ ID NO:2), in which at least one amino acid is in the D-isomeric form, and the amino acids are formed in the reverse order to the order found in the wild-type PSCK9 protein. In a related embodiment, the PCSK9 peptide of the vaccine constructs of the invention comprise an amino acid sequence derived from a portion of a mammalian PCSK9, preferably SEQ ID NO:1 or SEQ ID NO:2, in which all amino acids are in the D-isomeric form, and the amino acids are formed in the reverse order to the order found in the wild-type PSCK9 protein. In another embodiment, the PCSK9 peptide of the vaccine constructs of the invention comprise an amino acid sequence derived from a portion of a mammalian PCSK9, preferably SEQ ID NO:1 or SEQ ID NO:2, in which all amino acids are in the D-isomeric form, with the exception of at least one of the N-terminal and C-terminal amino acids, which are in the L-isomeric form, and the amino acids are formed in the reverse order to the order found in the wild-type PSCK9 protein. In a specific embodiment, the PCSK9 peptide of the vaccine constructs of the invention comprise an amino acid sequence derived from a portion of a mammalian PCSK9, preferably SEQ ID NO:1 or SEQ ID NO:2, in which all amino acids are in the D-isomeric form, with the exception of the N-terminal and C-terminal amino acids, which are in the L-isomeric form, and the amino acids are formed in the reverse order to the order found in the wild-type PSCK9 protein.

In another embodiment, the antigenic PCSK9 peptides of the present invention comprise amino acid variants derived from the PCSK9 amino acid fragment NVPEEDGTRFHRQASKC (SEQ ID NO:3) in the reverse order, made with D-amino acids with respect to at least one of the N and C-terminus amino acids. Thus, in one embodiment the PCSK9 peptide of the vaccine constructs of the invention comprise the amino acid sequence CKSAQRHFRTGDEEPVN (SEQ ID NO:4), in which at least one amino acid is in the D-isomeric form. In a related embodiment, the PCSK9 peptide of the vaccine constructs of the invention comprise the amino acid sequence CKSAQRHFRTGDEEPVN (SEQ ID NO:4), in which all amino acids are in the D-isomeric form. In another embodiment, the PCSK9 peptide of the vaccine constructs of the invention comprise the amino acid sequence CKSAQRHFRTGDEEPVN (SEQ ID NO:4), in which all amino acids are in the D-isomeric form, with the exception of at least one of the N-terminal and C-terminal amino acids, which are in the L-isomeric form. In a specific embodiment, the PCSK9 peptide of the vaccine constructs of the invention comprise the amino acid sequence CKSAQRHFRTGDEEPVN (SEQ ID NO:4), in which all amino acids are in the D-isomeric form, with the exception of the N-terminal and C-terminal amino acids, which are in the L-isomeric form.

The antigenic PCSK9 peptides disclosed herein encompass functionally active variant peptides derived from the amino acid sequence of PCSK9 in which amino acids have been deleted, inserted or substituted without essentially detracting from the immunological properties thereof, i.e. such functionally active variant peptides retain a substantial antigenic PCSK9 peptide biological activity.

In one embodiment, such functionally active variant peptides exhibit at least 60%, 65%, 70%, 75%, 80%, 85%, 90% or 95% identity to NVPEEDGTRFHRQASKC (SEQ ID NO:3), or at least 60%, 65%, 70%, 75%, 80%, 85%, 90% or 95% identity to CKSAQRHFRTGDEEPVN (SEQ ID NO:4). In another embodiment, such functionally active variant peptides exhibit at least 60%, 65%, 70%, 75%, 80%, 85%, 90% or 95% identity to NVPEEDGTRFHRQASKC (SEQ ID NO:3), or at least 60%, 65%, 70%, 75%, 80%, 85%, 90% or 95% identity to CKSAQRHFRTGDEEPVN (SEQ ID NO:4), and wherein at least one amino acid is in the D-isomeric form.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). An alternative algorithm when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997).

Functionally active variants comprise naturally occurring functionally active variants such as allelic variants and species variants and non-naturally occurring functionally active variants that can be produced by, for example, mutagenesis techniques or by direct synthesis.

A functionally active variant differs by about, for example, 1, 2, 3, 4 or 5 amino acid residues from NVPEEDGTRFHRQASKC (SEQ ID NO:3), and yet retains an antigenic PCSK9 biological activity. Where this comparison requires alignment, the sequences are aligned for maximum homology. The site of variation can occur anywhere in the peptide, as long as the biological activity is substantially similar to (SEQ ID NO: 3)
NVPEEDGTRFHRQASKC.

Guidance concerning how to make phenotypically silent amino acid substitutions is provided in Bowie et al., Science, 247: 1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions that are not critical for protein function. Thus, positions tolerating amino acid substitution can be modified while still maintaining specific immunogenic activity of the modified peptide.

The second strategy uses genetic engineering to introduce amino acid changes at specific positions of a cloned gene to identify regions critical for protein function. For example, site-directed mutagenesis or alanine-scanning mutagenesis can be used (Cunningham et al., Science, 244: 1081-1085 (1989)). The resulting variant peptides can then be tested for specific antigenic PCSK9 biological activity.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein are well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)).

Mutations can also be introduced using commercially available kits such as "QuikChange™ Site-Directed Mutagenesis Kit" (Stratagene™) or directly by peptide synthesis. The generation of a functionally active variant to an antigenic PCSK9 peptide by replacing an amino acid which does not significantly influence the function of the antigenic PCSK9 peptide can be accomplished by one skilled in the art.

A type of amino acid substitution that may be made in one of the peptides according to the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g. Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., (Science 256:1443-45 (1992)). A "moderately conservative" replacement is any change having a nonnegative value in the PAM250 log-likelihood matrix.

A functionally active variant peptide can also be isolated using a hybridization technique. Briefly, DNA having a high homology to the whole or part of a nucleic acid sequence encoding the peptide of interest, e.g. SEQ ID NOs: 1 to 4, is used to prepare a functionally active peptide. Therefore, an antigenic PCSK9 peptide of the invention also includes peptides which are functionally equivalent to one or more of the peptide of SEQ ID NOs: 1 to 4 and which are encoded by a nucleic acid molecule which hybridizes with a nucleic acid encoding any one of SEQ ID NOs: 1 to 4, or a complement thereof. One of skill in the art can easily determine nucleic acid sequences that encode peptides of the invention using readily available codon tables. As such, these nucleic acid sequences are not presented herein.

The stringency of hybridization for a nucleic acid encoding a peptide, polypeptide or protein that is a functionally active variant is, for example, 10% formamide, 5×SSPE, 1×Denhart's solution, and 1×salmon sperm DNA (low stringency conditions). More preferable conditions are, 25% formamide, 5×SSPE, 1×Denhart's solution, and 1×salmon sperm DNA (moderate stringency conditions), and even more preferable conditions are, 50% formamide, 5×SSPE, 1×Denhart's solution, and 1×salmon sperm DNA (high stringency conditions). However, several factors influence the stringency of hybridization other than the above-described formamide concentration, and one skilled in the art can suitably select these factors to accomplish a similar stringency.

Nucleic acid molecules encoding a functionally active variant can also be isolated by a gene amplification method such as PCR using a portion of a nucleic acid molecule DNA encoding a peptide, polypeptide or protein of interest.

In one embodiment of the invention, a peptide of the invention is derived from a natural source and isolated from a mammal, such as a human, a primate, a cat, a dog, a horse, a mouse, or a rat, preferably from a human source. A peptide of the invention can thus be isolated from cells or tissue sources using standard protein purification techniques. Alternatively, peptides of the invention can be synthesized chemically or produced using recombinant DNA techniques.

For example, a peptide of the invention can be synthesized by solid phase procedures well known in the art. Suitable syntheses may be performed by utilizing "T-boc" or "F-moc" procedures. Cyclic peptides can be synthesized by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989) and 'Methods in Molecular Biology, Vol. 35: Peptide Synthesis Protocols (ed. M. W. Pennington and B. M. Dunn), chapter 7, pp 91-171 by D. Andreau et al.

Alternatively, a polynucleotide encoding a peptide of the invention can be introduced into an expression vector that can be expressed in a suitable expression system using techniques well known in the art, followed by isolation or purification of the expressed peptide, polypeptide, or protein of interest. A variety of bacterial, yeast, plant, mammalian, and insect expression systems are available in the art and any such expression system can be used. Optionally, a polynucleotide encoding a peptide of the invention can be translated in a cell-free translation system.

Antigenic PCSK9 peptides of the invention can also comprise those that arise as a result of the existence of multiple genes, alternative transcription events, alternative RNA splicing events, and alternative translational and postranslational events. A peptide can be expressed in systems, e.g. cultured cells, which result in substantially the same postranslational modifications present as when the peptide is expressed in a native cell, or in systems that result in the alteration or omission of postranslational modifications, e.g. glycosylation or cleavage, present when expressed in a native cell.

An antigenic PCSK9 peptide of the invention can be produced as a fusion protein that contains other non-PCSK9 or non-PCSK9-derived amino acid sequences, such as amino acid linkers or signal sequences or immunogenic carriers as defined herein, as well as ligands useful in protein purification, such as glutathione-S-transferase, histidine tag, and staphylococcal protein A. More than one antigenic PCSK9 peptide of the invention can be present in a fusion protein. The heterologous polypeptide can be fused, for example, to the N-terminus or C-terminus of the peptide of the invention. A peptide of the invention can also be produced as fusion proteins comprising homologous amino acid sequences, i.e., other PCSK9 or PCSK9-derived sequences.

The antigenic PCSK9 peptides of the invention might be linear or conformationally constrained. As used herein in reference to a peptide, the term "conformationally constrained" means a peptide, in which the three-dimensional structure is maintained substantially in one spatial arrangement over time. Conformationally constrained molecules can have improved properties such as increased affinity, metabolic stability, membrane permeability or solubility.

In addition, such conformationally constrained peptides are expected to present the antigenic PCSK9 epitope in a conformation similar to their native loop conformation, thereby inducing anti-PCSK9 antibodies more susceptible to recognize intact, native self PCSK9 molecules or with an increased affinity to recognize self PCSK9 molecules. Methods of conformational constraint are well known in the art and include, without limitation, bridging and cyclization.

There are several approaches known in the prior art to introduce conformational constraints into a linear peptide. For example, bridging between two neighboring amino acids in a peptide leads to a local conformational modification, the flexibility of which is limited in comparison with that of regular peptides. Some possibilities for forming such bridges include incorporation of lactams and piperazinones (see, Giannis and Kolter, Angew. Chem. Int. Ed., 1993, 32: 1244).

Immunogenic Carrier of the Invention

In the vaccine constructs of the present invention, an antigenic PCSK9 peptide of the invention is linked to an immunogenic carrier molecule to form immunogens for vaccination protocols, preferably wherein the carrier molecule is not related to the native PCSK9 molecule.

The term "immunogenic carrier" herein includes those materials which have the property of independently eliciting an immunogenic response in a host animal and which can be covalently coupled to a peptide, polypeptide or protein either directly via formation of peptide or ester bonds between free carboxyl, amino or hydroxyl groups in the peptide, polypeptide or protein and corresponding groups on the immunogenic carrier material, or alternatively by bonding through a conventional bifunctional linking group, or as a fusion protein.

In specific embodiments, the immunogenic carrier is a virus-like particle (VLP), preferably a recombinant virus-like particle.

As used herein, the term "virus-like particle" refers to a structure resembling a virus particle but which has been demonstrated to be non pathogenic. In general, virus-like particles lack at least part of the viral genome. Also, virus-like particles can often be produced in large quantities by heterologous expression and can be easily purified. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage.

As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition, however, encompasses virus-like particles of bacteriophages, in which the aforementioned gene or genes are still present but inactive, and, therefore, also leading to non-replicative and noninfectious virus-like particles of a bacteriophage. The capsid structure formed from the self-assembly of subunits of RNA phage coat protein and optionally containing host RNA is herein referred to as a "VLP of RNA phage coat protein." Specific examples are the VLP of Qbeta, MS2, PP7 or AP205 coat proteins. In the specific case of Qbeta coat protein, for example, the VLP may either be assembled exclusively from Qbeta CP subunits (generated by expression of a Qbeta CP gene containing a TAA stop codon precluding any expression of the longer A1 protein through suppression (Kozlovska et al., 1996 Intervirology 39: 9-15), or additionally contain A1 protein subunits in the capsid assembly. Generally, the percentage of Qbeta A1 protein relative to Qbeta CP in the capsid assembly will be limited, in order to ensure capsid formation.

Examples of VLPs suitable as immunogenic carriers in the context of the present invention include, but are not limited to, VLPs of Qbeta, MS2, PP7, AP205 and other bacteriophage coat proteins, the capsid and core proteins of Hepatitis B virus (Ulrich, et al., Virus Res. 50: 141-182 (1998)), measles virus (Warnes, et al., Gene 160: 173-178 (1995)), Sindbis virus, rotavirus (U.S. Pat. Nos. 5,071,651 and 5,374,426), foot-and-mouth-disease virus (Twomey, et al., Vaccine 13: 1603-1610, (1995)), Norwalk virus (Jiang, X., et al., Science 250: 1580-1583 (1990); Matsui, S. M., et al., J. Clin. Invest. 87: 1456-1461 (1991)), the retroviral GAG protein (PCT Patent Appl. No. WO 96/30523), the retrotransposon Ty protein pl, the surface protein of Hepatitis B virus (WO 92/11291), human papilloma virus (WO 98/15631), human polyoma virus (Sasnauskas K., et al., Biol. Chem. 380 (3): 381-386 (1999); Sasnauskas K., et al., Generation of recombinant virus-like particles of different polyomaviruses in yeast. 3rd International Workshop "Virus-like particles as vaccines." Berlin, Sep. 26-29 (2001)), RNA phages, Ty, frphage, GA-phage, AP 205-phage and, in particular, Qbeta-phage, Cowpea chlorotic mottle virus, cowpea mosaic virus, human papilloma viruses (HPV), bovine papilloma viruses, porcine parvovirus, parvoviruses such as B19, porcine (PPV) and canine (CPV) parvovirues, caliciviruses (e.g. Norwalk virus, rabbit hemorrhagic disease virus [RHDV]), animal hepadnavirus core Antigen VLPs, filamentous/rod-shaped plant viruses, including but not limited to Tobacco Mosaic Virus (TMV), Potato Virus X (PVX), Papaya Mosaic Virus (PapMV), Alfalfa Mosaic Virus (AIMV), and Johnson Grass Mosaic Virus (JGMV), insect viruses such as flock house virus (FHV) and tetraviruses, polyomaviruses such as Murine Polyomavirus (MPyV), Murine Pneumotropic Virus (MPtV), BK virus (BKV), and JC virus (JCV).

As will be readily apparent to those skilled in the art, the VLP to be used as an immunogenic carrier of the invention is not limited to any specific form. The particle can be synthesized chemically or through a biological process, which can be natural or non-natural. By way of example, this type of embodiment includes a virus-like particle or a recombinant form thereof. In a more specific embodiment, the VLP can comprise, or alternatively consist of, recombinant polypeptides of any of the virus known to form a VLP. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts. Variant VLPs suitable for use in the present invention can be derived from any organism so long as they are able to form a "virus-like particle" and can be used as an "immunogenic carrier" as defined herein.

VLPs according to the invention may include the capsid protein or surface antigen of HBV (HBcAg and HBsAg respectively) or recombinant proteins or fragments thereof, and the coat proteins of RNA-phages or recombinant proteins or fragments thereof, more preferably the coat protein of Qbeta or recombinant proteins or fragments thereof. In one embodiment, the immunogenic carrier used in combination with an antigenic PCSK9 peptide of the invention is an HBcAg protein. Examples of HBcAg proteins that can be used in the context of the present invention can be readily determined by one skilled in the art. Examples include, but are not limited to, HBV core proteins described in Yuan et al., (J. Virol. 73: 10122-10128 (1999)), and in WO00/198333, WO 00/177158, WO 00/214478, WO WO00/32227, WO01/85208, WO02/056905, WO03/024480, and WO03/024481. HBcAgs suitable for use in the present invention can be derived from any organism so long as they are able to form a "virus-like particle" and can be used as an "immunogenic carrier" as defined herein.

In specific embodiments, the immunogenic carrier used in combination with an antigenic PCSK9 peptide or polypeptide of the invention is a Qbeta coat protein. Qbeta coat protein was found to self-assemble into capsids when expressed in *E. coli* (Kozlovska et al., 1993 Gene 137:133-137). The obtained capsids or virus-like particles showed an icosahedral phage-like capsid structure with a diameter of 25 nm and T=3 quasi symmetry. Further, the crystal structure of phage Qss has been solved. The capsid contains 180 copies of the coat protein, which are linked in covalent pentamers and hexamers by disulfide bridges (Golmohammadi et al., 1996 Structure 4: 5435554) leading to a remarkable stability of the capsid of Qbeta coat protein. Qbeta capsid protein also shows unusual resistance to organic solvents and denaturing agents. The high stability of the capsid of Qbeta coat protein is an advantageous feature, in particular, for its use in immunization and vaccination of mammals and humans in accordance of the present invention.

Examples of Qbeta coat proteins that can be used in the context of the present invention can be readily determined by one skilled in the art. Examples have been extensively described in WO02/056905, WO03/024480, WO03/024481 (incorporated herein by reference in their entirety) and include, but are not limited to, amino acid sequences disclosed in PIR database, accession No. VCBPQbeta referring to Qbeta CP; Accession No. AAA16663 referring to Qbeta A1 protein; and variants thereof including variants proteins in which the N-terminal methionine is cleaved; C-terminal truncated forms of Qbeta A1 missing as much as 100, 150 or 180 amino acids; variant proteins which have been modified by the removal of a lysine residue by deletion or substitution or by the addition of a lysine residue by substitution or insertion (see for example Qbeta-240, Qbeta-243, Qbeta-250, Qbeta-251 and Qbeta-259 disclosed in PCT publication No. WO 03/024481, incorporated by reference in its entirety), and variants exhibiting at least 80%, 85%, 90%, 95%, 97%, or 99% identity to any of the Qbeta core proteins described above. Variant Qbeta coat proteins suitable for use in the present invention can be derived from any organism so long as they are able to form a "virus-like particle" and can be used as "immunogenic carriers" as defined herein.

Linker Constructs of the Invention

The antigenic PCSK9 peptides of the invention may be coupled to immunogenic carriers via chemical conjugation or by expression of genetically engineered fusion partners. The coupling does not necessarily need to be direct, but can occur through linker sequences. More generally, in the case that antigenic peptides either fused, conjugated or otherwise attached to an immunogenic carrier, spacer or linker sequences are typically added at one or both ends of the antigenic peptides. Such linker sequences generally comprise sequences recognized by the proteasome, proteases of the endosomes or other vesicular compartment of the cell.

In one embodiment, the peptides of the present invention are expressed as fusion proteins with the immunogenic carrier. Fusion of the peptide can be effected by insertion into the immunogenic carrier primary sequence, or by fusion to either the N- or C-terminus of the immunogenic carrier. Hereinafter, when referring to fusion proteins of a peptide to an immunogenic carrier, the fusion to either ends of the subunit sequence or internal insertion of the peptide within the carrier sequence are encompassed. Fusion, as referred to hereinafter, may be effected by insertion of the antigenic peptide into the sequence of the carrier, by substitution of part of the sequence of the carrier with the antigenic peptide, or by a combination of deletion, substitution or insertions.

When the immunogenic carrier is a VLP, the chimeric antigenic peptide-VLP subunit will be in general capable of self-assembly into a VLP. VLP displaying epitopes fused to their subunits are also herein referred to as chimeric VLPs. For example, EP 0 421 635 B describes the use of chimeric hepadnavirus core antigen particles to present foreign peptide sequences in a virus-like particle.

Flanking amino acid residues may be added to either end of the sequence of the antigenic peptide to be fused to either end of the sequence of the subunit of a VLP, or for internal insertion of such peptide sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In another specific embodiment of the invention, the immunogenic carrier is a VLP of a RNA phage, preferably Qbeta. The major coat proteins of RNA phages spontaneously assemble into VLPs upon expression in bacteria, and in particular in E. coli. Fusion protein constructs wherein antigenic peptides have been fused to the C-terminus of a truncated form of the A1 protein of Qbeta, or inserted within the A1 protein have been described (Kozlovska, T. M., et al., Intervirology, 39: 9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qbeta CP gene) usually takes place in E. coli, and such is the case for N-termini of the Qbeta coat proteins. The part of the A1 gene, 3' of the UGA amber codon encodes the CP extension, which has a length of 195 amino acids. Insertion of the antigenic peptide between position 72 and 73 of the CP extension leads to further embodiments of the invention (Kozlovska, T. M., et al., Intervirology 39: 9-15 (1996)). Fusion of an antigenic peptide at the C-terminus of a C-terminally truncated Qbeta A1 protein leads to further preferred embodiments of the invention. For example, Kozlovska et al., (Intervirology, 39: 9-15 (1996)) describe Qbeta A1 protein fusions where the epitope is fused at the C-terminus of the Qbeta CP extension truncated at position 19.

As described by Kozlovska et al. (supra), assembly of the particles displaying the fused epitopes typically requires the presence of both the A1 protein-antigen fusion and the wt CP to form a mosaic particle. However, embodiments comprising virus-like particles, and hereby in particular the VLPs of the RNA phage Qbeta coat protein, which are exclusively composed of VLP subunits having an antigenic peptide fused thereto, are also within the scope of the present invention.

The production of mosaic particles may be effected in a number of ways. Kozlovska et al. (supra), describe three methods, all of which can be used in the practice of the invention. In the first approach, efficient display of the fused epitope on the VLPs is mediated by the expression of the plasmid encoding the Qbeta A11 protein fusion having a UGA stop codon between CP and CP extension in an E. coli strain harboring a plasmid encoding a cloned UGA suppressor tRNA which leads to translation of the UGA codon into Trp (pISM3001 plasmid (Smiley et al. 1993 Gene 134:33-40). In another approach, the CP gene stop codon is modified into UAA, and a second plasmid expressing the A1 protein-antigen fusion is co-transformed. The second plasmid encodes a different antibiotic resistance and the origin of replication is compatible with the first plasmid. In a third approach, CP and the A1 protein-antigen fusion are encoded in a bicistronic manner, operatively linked to a promoter such as the Trp promoter, as described in FIG. 1 of Kozlovska et al., 1996 Intervirology 39:9-15. Further VLPs suitable for fusion of antigens or antigenic determinants are described in WO 03/024481 and include bacteriophage fr, RNA phase MS-2, capsid protein of papillomavirus, retrotransposon Ty, yeast and also Retrovirus-like-particles, HIV2 Gag, Cowpea Mosaic Virus, parvovirus VP2 VLP, HBsAg (U.S. Pat. No. 4,722,840, EP0020416B1). Examples of chimeric VLPs suitable for the practice of the invention are also those described in Intervirology 39: 1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus.

In a preferred embodiment, a vaccine construct containing the PCSK9 peptide representing amino acids 207-223 of human PCSK9 (SEQ ID NO:3) is synthesized by conjugating the peptide to Qbeta bacteriophage VLPs using a bifunctional cross-linker (SMPH) with amine- and sulfhydryl-reactive arms. This cross-linker conjugates free amines on the surface of the Q-beta VLPs to the sulfhydryl group found in C-terminal cysteine residue of the PCSK9 peptide. In this synthesis methodology, the Q-beta VLP is purified from free, unconjugated crosslinker, and then reacted with the PCSK9 peptide at a molar ratio of about 10 peptide:1 VLP).

For any recombinantly expressed antigenic PCSK9 peptide according to the invention (whether or not coupled to an immunogenic carrier), the nucleic acid which encodes the peptide or protein is also an aspect of the present invention, as is an expression vector comprising the nucleic acid, and a host cell containing the expression vector (autonomously or chromosomally inserted). A method of recombinantly producing the peptide or protein by expressing it in the above host cell and isolating the immunogen therefrom is a further aspect of the invention.

In another embodiment, the peptide of the invention is chemically coupled to an immunogenic carrier, using techniques well known in the art. Conjugation can occur to allow free movement of peptides via single point conjugation (e.g. either N-terminal or C-terminal point) or as a locked down structure where both ends of peptides are conjugated to either an immunogenic carrier protein or to a scaffold structure such as a VLP. Conjugation occurs via conjugation chemistry known to those skilled in the art such as via cysteine residues, lysine residues or other carboxy moiety's commonly known as conjugation points such as glutamic acid or aspartic acid. Thus, for example, for direct covalent coupling it is possible to utilize a carbodiimide, glutaraldehyde or N-[y-maleimidobutyryloxy] succinimide ester, utilizing common commercially available hetero-bifunctional linkers such as CDAP and SPDP. Examples of conjugation of peptides, particularly cyclized peptides, to a protein carrier via acylhydrazine peptide derivatives are described in WO 03/092714. After the coupling reaction, the immunogen can easily be isolated and purified by means of a dialysis method, a gel filtration method, a fractionation method etc. Peptides terminating with a cysteine residue (preferably with a linker outside the cyclized region) may be conveniently conjugated to a carrier protein via maleimide chemistry.

When the immunogenic carrier is a VLP, several antigenic peptides, either having an identical amino acid sequence or a different amino acid sequence, may be coupled to a single VLP molecule, leading preferably to a repetitive and ordered structure presenting several antigenic determinants in an oriented manner as described in WO00/32227, WO03/024481, WO02/056905 and WO04/007538.

In a preferred embodiment, the antigenic PCSK9 peptide is bound to the VLP by way of chemical cross-linking, typically using a hetero-bifunctional cross-linker. Several hetero-bifunctional cross-linkers are known to the art. In some embodiments, the hetero-bifunctional crosslinker contains a functional group which can react with first attachment sites, i.e. with the side-chain amino group of lysine residues of the VLP or VLP subunit, and a further functional group which can react with a preferred second attachment site, i.e. a cysteine residue fused to the antigenic peptide and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigenic peptide is reacted with the activated VLP, and this step is typically called the coupling step. Unreacted antigenic peptide may be optionally removed in a fourth step, for example by dialysis. Several heterobifunctional crosslinkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage.

Another class of cross-linkers suitable in the practice of the invention is characterized by the introduction of a disulfide linkage between the antigenic peptide and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of antigenic peptide per subunits of the VLP can be adjusted by varying the experimental conditions described above to match the requirements of the vaccine.

Another method of binding antigenic peptides to the VLP is the linking of a lysine residue on the surface of the VLP with a cysteine residue on the antigenic peptide. In some embodiments, fusion of an amino acid linker containing a cysteine residue, as a second attachment site or as a part thereof, to the antigenic peptide for coupling to the VLP may be required. In general, flexible amino acid linkers are favored. Examples of the amino acid linker are selected from the group consisting of: (a) CGG; (b) N-terminal gamma 1-linker; (c) N-terminal gamma 3-linker; (d) Ig hinge regions; (e) N-terminal glycine linkers; (f)(G) kC (G) n with n=0-12 and k=0-5; (g) N-terminal glycine-serine linkers; (h) (G) kC (G) m (S) i (GGGGS) n with n=0-3, k=0-5, m=0-10, i=0-2; (i) GGC; (k) GGC-NH2; (l) C-terminal gamma 1-linker; (m) C-terminal gamma 3-linker; (n) C-terminal glycine linkers; (o) (G)nC (G) k with n=0-12 and k=0-5; (p) C-terminal glycine-serine linkers; (q) (G) m (S) t (GGGGS) n (G) oC (G) k with n=0-3, k=0-5, m=0-10, 1=0-2, and o=0-8. Further examples of amino acid linkers are the hinge region of immunoglobulins, glycine serine linkers (GGGGS)n, and glycine linkers (G)n all further containing a cysteine residue as second attachment site and optionally further glycine residues. Preferred examples of the amino acid linkers are N-terminal gamma 1: CGDKTHTSPP; C-terminal gamma 1: DKTHTSPPCG; N-terminal gamma 3: CGGPKPSTPPGSSGGAP; C-terminal gamma 3: PKP-STPPGSSGGAPGGCG; N-terminal glycine linker: GCGGGG and C-terminal glycine linker: GGGGCG.

Other amino acid linkers particularly suitable in the practice of the invention, when a hydrophobic antigenic peptide is bound to a VLP, are CGKKGG, or CGDEGG for N-terminal linkers, or GGKKGC and GGEDGC, for the C-terminal linkers. For the C-terminal linkers, the terminal cysteine is optionally C-terminally amidated.

In some embodiments of the present invention, GGCG, GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In a further embodiment of the invention, the amino acid linker GGC-NH2 is fused to the C-terminus of the antigenic peptide.

The cysteine residue present on the antigenic peptide has to be in its reduced state to react with the hetero-bifunctional cross-linker on the activated VLP, that is a free cysteine or a cysteine residue with a free sulfhydryl group has to be available. In the instance where the cysteine residue functions as a binding site, is in an oxidized form, for example if it is forming a disulfide bridge, reduction of this disulfide bridge with e.g. DTT, TCEP or p-mercaptoethanol is required. Low concentrations of reducing agent are compatible with coupling as described in WO 02/05690, higher concentrations inhibit the coupling reaction, as a skilled artisan would know, in which case the reductant has to be removed or its concentration decreased prior to coupling, e.g. by dialysis, gel filtration or reverse phase HPLC.

Binding of the antigenic peptide to the VLP by using a hetero-bifunctional cross-linker according to the methods described above, allows coupling of the antigenic peptide to the VLP in an oriented fashion. Other methods of binding the antigenic peptide to the VLP include methods wherein the antigenic peptide is cross-linked to the VLP using the carbodiimide EDC, and NHS.

In other methods, the antigenic peptide is attached to the VLP using a homo-bifunctional cross-linker such as glutaraldehyde, DSGBM [PEO]-4, BS3, (Pierce Chemical Company, Rockford, Ill., USA) or other known homo-bifunctional cross-linkers with functional groups reactive towards amine groups or carboxyl groups of the VLP.

Other methods of binding the VLP to an antigenic peptide include methods where the VLP is biotinylated, and the antigenic peptide expressed as a streptavidin-fusion protein, or methods wherein both the antigenic peptide and the VLP are biotinylated, for example as described in WO 00/23955. In this case, the antigenic peptide may be first bound to streptavidin or avidin by adjusting the ratio of antigenic peptide to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigenic peptide, may be used as binding agents for binding antigenic peptide to the VLP. Alternatively, either the ligand or the receptor may be fused to the antigenic peptide, and thereby mediate binding to the VLP chemically bound or fused either to the receptor, or the ligand respectively. Fusion may also be effected by insertion or substitution.

One or several antigen molecules can be attached to one subunit of the capsid or VLP of RNA phage coat proteins, preferably through the exposed lysine residues of the VLP of RNA phages, if sterically allowable. A specific feature of the VLP of the coat protein of RNA phages and in particular of the QP coat protein VLP is thus the possibility to couple several antigens per subunit. This allows for the generation of a dense antigen array. VLPs or capsids of Q coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In a further embodiment of the present invention, the first attachment site is a lysine residue and/or the second attachment comprises sulfhydryl group or a cysteine residue. In an even further embodiment of the present invention, the first attachment site is a lysine residue and the second attachment is a cysteine residue. In further embodiments of the invention, the antigen or antigenic determinant is bound via a cysteine residue, to lysine residues of the VLP of RNA phage coat protein, and in particular to the VLP of Qbeta Coat Protein.

Another advantage of the VLPs derived from RNA phage is their high expression yield in bacteria that allows production of large quantities of material at affordable cost. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qbeta coat protein allows a very high antigen density to be achieved.

According to an embodiment of the present invention the antigenic PCSK9 peptide disclosed herein are linked, preferably chemically cross linked, to Qbeta, either directly or via one of the peptide linker disclosed herein, to generate an immunogen. In an embodiment, the antigenic PCSK9 peptide disclosed herein is linked to Qbeta by way of chemical cross-linking as described herein and preferably using a hetero-bifunctional cross-linker, as disclosed above.

Preferred hetero-bifunctional cross-linkers for use with CRM197 are BAANS (bromoacetic acid N-hydroxysuccinimide ester), SMPH (Succinimidyl-6-[β-maleimidopropionamido]hexanoate), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA). In a preferred embodiment of the present invention, the hetero-bifunctional crosslinker is BAANS or SMPH. Alternatively, cross-linkers suitable allowing the introduction of a disulfide linkage between the antigenic peptide and Qbeta could also be used in the context of the invention. Preferred cross-linkers belonging to this class include for example SPDP and Sulfo-LC-SPDP (Pierce).

In a particular embodiment, when the sequence of the antigenic PCSK9 peptide comprises a cysteine, the antigenic PCSK9 peptide may be covalently linked to Qbeta directly via the cysteine.

In some embodiments of the invention, immunogenic compositions of the invention may comprise mixtures of immunogenic conjugates, i.e. immunogenic carriers coupled to one or several antigenic PCSK9 peptides of the invention. Thus, these immunogenic compositions may be composed of immunogenic carriers which differ in amino acid sequence. For example, vaccine compositions could be prepared comprising a "wild-type" VLP and a modified VLP protein in which one or more amino acid residues have been altered (e.g., deleted, inserted or substituted). Alternatively, the same immunogenic carrier might be used but coupled to antigenic PCSK9 peptides of different amino acid sequences.

The invention therefore also relates to methods for producing an immunogen according to the invention comprising i) providing an antigenic PCSK9 peptide according to the invention, ii) providing an immunogenic carrier according to the invention, preferably a VLP, and iii) combining the antigenic PCSK9 peptide and the immunogenic carrier. In one embodiment, the combining step occurs through chemical cross-linking, preferably through a hetero-bifunctional cross-linker.

In an embodiment of the present invention the antigenic PCSK9 peptide disclosed herein further comprise either at its N-terminus, or at its C-terminus or at both the N-terminus and C-terminus a linker which is able to react with an attachment site of the immunogenic carrier in a chemical cross-linking reaction. In an embodiment, the antigenic PCSK9 peptide disclosed herein further comprise at its C-terminus a linker having the formula (G)nC, (G)nSC or (G)nK, preferably (G)nC wherein n is an integer between 0-10, preferably 0-5, more preferably 0, 1, 2 or 3. Most preferably, n is 0 or 1 (where n is equal to 0 the formula represents a cysteine). Preferably the antigenic PCSK9 peptide disclosed herein further comprise at its C-terminus a linker having the formula GGGC, GGC, GC or C.

In another embodiment of the present invention the antigenic PCSK9 peptide disclosed herein further comprise at its N-terminus a linker having the formula C(G)n, CS(G)n or K(G)n, preferably C(G)n wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic PCSK9 peptide disclosed herein further comprise at its N-terminus a linker having the formula CGGG, CGG, CG or C.

In another embodiment the antigenic PCSK9 peptide disclosed herein further comprise at its C-terminus a linker having the formula (G)nC, (G)nSC or (G)nK, preferably (G)nC wherein n is an integer of 0-10, preferably 0, 1, 2, 3, 4 and 5, more preferably 0, 1, 2 and 3, most preferably, n is 0 or 1 (where n is equal to 0 the formula represents a cysteine) and at its N-terminus a linker having the formula C(G)n, CS(G)n or K(G)n, preferably C(G)n wherein n is an integer of 0-10, preferably 0, 1, 2, 3, 4 and 5, more preferably 0, 1, 2 and 3, most preferably, n is 0 or 1 (where n is equal to 0, the formula represents a cysteine). Preferably the antigenic PCSK9 peptide disclosed herein further comprise at its N-terminus a linker having the formula CGGG, CGG, CG or C and at its C-terminus a linker having the formula GGGC, GGC, GC or C. Preferably, the antigenic PCSK9 peptide disclosed herein further comprises at its N-terminus a cysteine and at its C-terminus a cysteine.

In one embodiment, the antigenic PCSK9 peptide is cyclized. In one embodiment, the cyclized antigenic PCSK9 peptide is attached to an immunogenic carrier. In one embodiment, the cyclized antigenic PCSK9 peptide is attached to an immunogenic carrier by covalent binding. In one embodiment, the cyclized antigenic PCSK9 peptide is attached to an immunogenic carrier by covalent binding of one of the side chain of its amino acids to the carrier. In one embodiment, a cysteine, a GC or a CC fragment comprising a variable number of glycine residues and one cysteine residue is added to the cyclized PCSK9 peptides to enable the covalent binding to the immunogenic carrier through the added cysteine.

In one embodiment, the antigenic PCSK9 peptide is cyclized and comprises a cysteine, a (G)nC or a C(G)n fragment wherein n is 0, 1, 2, 3, 4, 5, 6, 7, 8, 9 and 10, preferably 0, 1, 2, 3, 4 and 5, more preferably 0, 1, 2 and 3, most preferably, n is 0 or 1 (where n is equal to 0, the formula represents a cysteine).

Compositions Comprising an Antigenic PCSK9 Peptide of the Invention

The present invention further relates to compositions, particularly immunogenic compositions comprising an antigenic PCSK9 peptide linked to an immunogenic carrier, and optionally at least one adjuvant. Such immunogenic compositions are useful to prevent, treat or alleviate PCSK9-related disorders.

In some embodiments, an immunogenic composition according to the invention comprises an antigenic PCSK9 peptide, optionally comprising a linker, linked to an immunogenic carrier, selected from Qbeta, DT, PP7, PPV or Norwalk Virus VLP.

In a preferred embodiment, an immunogenic composition according to the invention comprises an antigenic PCSK9 peptide, optionally comprising a linker, linked to a Qbeta VLP.

In some embodiments, a subject immunogenic composition comprises single species of antigenic PCSK9 peptide, e.g., the immunogenic composition comprises a population of antigenic PCSK9 peptides, substantially all of which have the same amino acid sequence. In other embodiments, a subject immunogenic composition comprises two or more different antigenic PCSK9 peptides, e.g., the immunogenic composition comprises a population of antigenic PCSK9 peptides, the members of which population can differ in amino acid sequence. A subject immunogenic composition can comprise from two to about 20 different antigenic PCSK9 peptides, e.g., a subject immunogenic composition can comprise 2, 3, 4, 5, 6, 7, 8, 9, 10, 11-15, or 15-20 different antigenic PCSK9 peptides, each having an amino acid sequence that differs from the amino acid sequences of the other antigenic PCSK9 peptides.

In other embodiments, a subject immunogenic composition comprises a multimerized antigenic PCSK9 polypeptide, as described above. As used herein, the terms "immunogenic composition comprising an antigenic PCSK9 peptide" or "immunogenic composition of the invention" or "subject immunogenic composition" refers to an immunogenic composition comprising either single species (multimerized or not) or multiple species of antigenic PCSK9 peptide(s) coupled or not to an immunogenic carrier. Where two or more peptides are used coupled to a carrier, the peptide may be coupled to the same carrier molecule or individually coupled to carrier molecules and then combined to produce an immunogenic composition.

Another aspect of the invention relates to methods for producing an immunogen according to the invention, the method comprising coupling an antigenic PCSK9 peptide to an immunogenic carrier. In one embodiment, the coupling is chemical.

Adjuvants

In some embodiments, a subject immunogenic composition comprises at least one adjuvant. Suitable adjuvants include those suitable for use in mammals, preferably in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al. (1998) J. Leukocyte Biol. 64:713; WO90/03184, WO96/11711, WO 00/48630, WO98/36772, WO00/41720, WO06/134423 and WO07/026,190), LT/CT mutants, poly(D,L-lactide-co-glycolide) (PLG) microparticles, Quil A, TiterMax classic, TiterMax Gold, interleukins, and the like. For veterinary applications including but not limited to animal experimentation, one can use Freund's adjuvant, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in Vaccine design: the subunit and adjuvant approach, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg Vaccine 2000, 19, 618-622; Krieg Curr opin Mol Ther2001 3:15-24; Roman et al., Nat. Med., 1997, 3, 849-854; Weiner et al., PNAS USA, 1997, 94, 10833-10837; Davis et al, J. Immunol, 1998, 160, 870-876; Chu et al., J. Exp. Med, 1997, 186, 1623-1631; Lipford et al, Ear. J. Immunol., 1997, 27, 2340-2344; Moldoveami et al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157,2116-2122; Messina et al, J. Immunol, 1991, 147, 1759-1764; Yi et al, J. Immunol, 1996, 157,4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition, such as Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. as described in Kanzler et al 2007, Nature Medicine 13, p1552-9), including TLR3 ligands such as polyI:C and similar compounds such as Hiltonol and Ampligen.

In a particular embodiment, the adjuvant is an immunostimulatory oligonucleotide and more preferably a CpG oligonucleotide. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail below. Methods of the invention embrace the use of these different classes of CpG immunostimulatory oligonucleotides.

Any of the classes may be subjugated to an E modification that enhances its potency. An E modification may be a halogen substitution for the 5' terminal nucleotide; examples of such substitutions include but are not limited to bromo-uridine or iodo-uridine substitutions. An E modification can also include an ethyl-uridine substitution for the 5' terminal nucleotide.

The "A class" CpG immunostimulatory oligonucleotides are characterized functionally by the ability to induce high levels of interferon-alpha (IFN-α) from plasmacytoid dendritic cells (pDC) and inducing NK cell activation while having minimal effects on B cell activation. Structurally, this class typically has stabilized poly-G sequences at 5' and 3' ends. It also has a palindromic phosphodiester CpG dinucleotide-containing sequence of at least 6 nucleotides, for example but not necessarily, it contains one of the following hexamer palindromes: GACGTC, AGCGCT, or AACGTT described by Yamamoto and colleagues (Yamamoto, S., et al. J. Immunol. 148:4072-6 (1992). A class CpG immunostimulatory oligonucleotides and exemplary sequences of this class have been described in U.S. Pat. No. 6,949,520 and published PCT application PCT/US00/26527 (WO 01/22990), both filed on Sep. 27, 2000.

Pharmaceutical Compositions of the Invention

The invention also provides pharmaceutical compositions comprising an antigenic PCSK9 peptide of the invention or an immunogenic composition thereof, in a formulation in association with one or more pharmaceutically acceptable excipient(s) and optionally combined with one or more adjuvants, as described above. The term 'excipient' is used herein to describe any ingredient other than the active ingredient, i.e. the antigenic PCSK9 peptide of the invention eventually coupled to an immunogenic carrier and optionally combined with one or more adjuvants. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the active ingredient.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, or proteins accepted in the art may suitably be employed for the peptides or proteins of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous, subcutaneous, intradermal and intramuscular routes, even more preferred embodiments are the intramuscular or the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, microparticles, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-PCSK9 peptide, preferably coupled to an immunogenic carrier, optionally in combination with one or more adjuvants, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 0.1 mg/mL to about 20 mg/mL of a peptide of the invention, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

The antigenic PCSK9 peptides of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurized container, pump, spray, atomizer (preferably an atomizer using electrohydrodynamics to produce a fine mist), or nebulizer, with or without the use of a suitable propellant, or as nasal drops.

The pressurized container, pump, spray, atomizer, or nebulizer generally contains a solution or suspension of an antibody of the invention comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the compound of the invention, a suitable powder base and a performance modifier.

A suitable solution formulation for use in an atomizer using electrohydrodynamics to produce a fine mist may contain a suitable dose of the antigenic PCSK9 peptide of the invention per actuation and the actuation volume may vary from 1 μL to 100 μL.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

A pharmaceutical composition comprising an antigenic PCSK9 peptide may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compositions of the invention can be used to treat, alleviate or prevent PCSK9-mediated disorders or symptoms in a subject at risk or suffering from such disorder or symptom by stimulating an immune response in the subject by immunotherapy. Immunotherapy can comprise an initial immunization followed by additional, e.g. one, two, three, or more boosters.

An "immunologically effective amount" of an antigenic PCSK9 peptide of the invention, or composition thereof, is an amount that is delivered to a mammalian subject, either in a single dose or as part of a series, which is effective for inducing an immune response against PCSK9 in the subject. This amount varies depending upon the health and physical condition of the individual to be treated, the taxonomic group of individual to be treated, the capacity of the individual's immune system to synthesize antibodies, the formulation of the vaccine, and other relevant factors. It is expected that the amount will fall in a relatively broad range that can be determined through routine trials.

A "pharmaceutically effective dose" or "therapeutically effective dose" is that dose required to treat or prevent, or alleviate one or more PCSK9-related disorder or symptom in a subject. The pharmaceutically effective dose depends on inter alia the specific compound to administer, the severity of the symptoms, the susceptibility of the subject to side effects, the type of disease, the composition used, the route of administration, the type of mammal being treated, the physical characteristics of the specific mammal under consideration such as health and physical condition, concurrent medication, the capacity of the individual's immune system to synthesize antibodies, the degree of protection desired, and other factors that those skilled in the medical arts will recognize. For prophylaxis purposes, the amount of peptide in each dose is selected as an amount which induces an immunoprotective response without significant adverse side effects in typical vaccines. Following an initial vaccination, subjects may receive one or several booster immunizations adequately spaced.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For example, antigenic PCSK9 peptides or pharmaceutical composition of the invention can be administered to a subject at a dose of about 0.1 μg to about 5 mg, e.g., from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, from about 1 mg to about 2 mg, with optional boosters given at, for example, 1 week, 2 weeks, 3 weeks, 4 weeks, two months, three months, 6 months and/or a year later.

In some embodiments, a single dose of an antigenic PCSK9 peptide or pharmaceutical composition according to the invention is administered. In other embodiments, multiple doses of an antigenic PCSK9 peptide or pharmaceutical composition according to the invention are administered. The frequency of administration can vary depending on any of a variety of factors, e.g., severity of the symptoms, degree of immunoprotection desired, whether the composition is used for prophylactic or curative purposes, etc. For example, in some embodiments, an antigenic PCSK9 peptide or pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). When the composition of the invention is used for prophylaxis purposes, they will be generally administered for both priming and boosting doses. It is expected that the boosting doses will be adequately spaced, or preferably given yearly or at such times where the levels of circulating antibody fall below a desired level. Boosting doses may consist of the antigenic PCSK9 peptide in the absence of the original immunogenic carrier molecule. Such booster constructs may comprise an alternative immunogenic carrier or may be in the absence of any carrier. Such booster compositions may be formulated either with or without adjuvant.

The duration of administration of an antigenic PCSK9 peptide according to the invention, e.g., the period of time over which an antigenic PCSK9 peptide is administered, can vary, depending on any of a variety of factors, e.g., patient response, etc. For example, an antigenic PCSK9 peptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A variety of treatment methods are also contemplated by the present disclosure, which methods comprise administering an antigenic PCSK9 peptide according to the invention. Subject treatment methods include methods of inducing an immune response in an individual to self-PCSK9, and methods of preventing, alleviating or treating a PCSK9-related disorder or symptom in an individual.

In one aspect, the present invention provides a method for treating, preventing or alleviating a PCSK9-related disorder or symptom in a subject, comprising administering a therapeutically effective amount of an antigenic PCSK9 peptide of the invention, or immunogenic or pharmaceutical composition thereof, to the subject.

In another aspect, the present invention provides a method for inducing an immune response against self-PCSK9 in a subject, comprising administering a therapeutically or immunogenically effective amount of an antigenic PCSK9 peptide of the invention, or immunogenic or pharmaceutical composition thereof, to the subject.

A PCSK9 related disease or a PCSK9 mediated disease is, for example, a disease where the inhibition of PCSK9 activity or the inhibition of the interaction of PCSK9 with the LDL receptor could be beneficial.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. The subject is preferably human, and may be either male or female, of any age.

Other aspects of the invention relate to an antigenic PCSK9 peptide according to the invention or of an immunogenic composition or a pharmaceutical composition thereof, for use as a medicament, preferably in treatment, alleviation or prophylaxis of PCSK9-related disorders.

In yet another aspect, the present invention provides the use of an antigenic PCSK9 peptide of the invention or of an immunogenic composition or a pharmaceutical composition thereof, in the manufacture of a medicament, preferably for treating a PCSK9-related disorder.

In particular, the invention relates to an antigenic PCSK9 peptide of the invention, or an immunogenic or pharmaceutical composition thereof, for use as a medicament preferably in treatment, alleviation or prophylaxis of diseases associated with an elevated level of cholesterol.

In yet another aspect, the present invention provides the use of an antigenic PCSK9 peptide of the invention or of an immunogenic composition or a pharmaceutical composition thereof, in the manufacture of a medicament, preferably for lowering the LDL-cholesterol level in blood in a subject in need thereof.

In some aspects of the uses or methods of the invention, the PCSK9-related disorder is selected from the group consisting of elevated cholesterol, a condition associated with elevated LDL-cholesterol, e.g., a lipid disorder (e.g., hyperlipidemia, type I, type II, type III, type IV, or type V hyperlipidemia, secondary hypertriglyceridemia, hypercholesterolemia, familial hypercholesterolemia, xanthomatosis, lecithin:cholesterol acetyltransferase deficiency), arteriosclerotic conditions (e.g., atherosclerosis), coronary artery disease, and cardiovascular disease.

In yet another aspect, the present invention provides the use of an antigenic PCSK9 peptide of the invention or of an immunogenic composition or a pharmaceutical composition thereof, in the manufacture of a medicament for treating or alleviating diseases where an up-regulation of the LDL receptor or an inhibition of the interaction between PCSK9 and the LDL receptor is beneficial.

In yet another aspect, the present invention provides the use of an antigenic PCSK9 peptide of the invention or of an immunogenic composition or a pharmaceutical composition thereof, in the manufacture of a medicament for the treatment of Alzheimer's disease.

In other aspects of the uses or methods of the invention, the subject is a mammal, preferably a human subject.

In still other aspects of the uses or methods of the invention, the subject suffers from the PSCK9-related disorder. Alternatively, the subject is at risk of suffering from the PCSK9-related disorder, e.g., due to the presence of one or more risk factors (e.g., hypertension, cigarette smoking, diabetes, obesity, or hyperhomocysteinemia).

The antigenic PCSK9 peptide of the invention or an immunogenic composition or a pharmaceutical composition thereof are useful for subjects who are intolerant to therapy with another cholesterol-reducing agent, or for whom therapy with another cholesterol-reducing agent has produced inadequate results (e.g., subjects who experience insufficient LDL-c reduction on statin therapy). The antigenic PCSK9 peptide of the invention described herein can be administered to a subject with elevated LDL-cholesterol.

Preferably a subject with elevated cholesterol is a human subject with total plasma cholesterol levels of 200 mg/dl or greater. Preferably a subject with elevated cholesterol is a human subject with LDL-cholesterol levels of 160 mg/dl or greater.

Total plasma cholesterol levels and LDL-cholesterol levels are measured using standard methods on blood samples obtained after an appropriate fast. Protocols to measure total plasma cholesterol levels and LDL-cholesterol levels are well-known to persons skilled in the art.

In one embodiment the antigenic PCSK9 peptide or an immunogenic composition or a pharmaceutical composition thereof is administered together with another agent, the two can be administered sequentially in either order or simultaneously. In some embodiments, an antigenic PCSK9 peptide or an immunogenic composition or a pharmaceutical composition thereof is administered to a subject who is also receiving therapy with a second agent (e.g., a second cholesterol-reducing agent). Cholesterol reducing agents include statins, bile acid sequestrants, niacin, fibric acid derivatives, and long chain alpha, omego-dicarboxylic acids. Statins inhibit cholesterol synthesis by blocking HMGCoA, a key enzyme in cholesterol biosynthesis. Examples of statins are lovastatin, pravastatin, atorvastatin, cerivastatin, fluvastatin, and simvastatin. The inventors' data demonstrates an unexpected synergistic effect in the combined administration of a statin and the immunization with the PCSK9 peptide—VLP constructs of this disclosure. Bile acid sequestrants interrupt the recycling of bile acids from the intestine to the liver. Examples of these agents are cholestyramine and colestipol hydrochloride. Examples of fibric acid derivatives are clofibrate and gemfibrozil. The combined administration of a fibric acid derivative, a statin, and immunization with the PCSK9 peptide—VLP constructs of this disclosure is also contemplated for patients in need of such therapy. Long chain alpha, omego-dicarboxylic acids are described, e.g., by Bisgaier et al., 1998, J. Lipid Res. 39:17-30; WO 98/30530; U.S. Pat. No. 4,689,344; WO 99/001 16; U.S. Pat. No. 5,756,344; U.S. Pat. No. 3,773,946; U.S. Pat. No. 4,689,344; U.S. Pat. No. 4,689,344; U.S. Pat. No. 4,689,344; and U.S. Pat. No. 3,930,024); ethers (see, e.g., U.S. Pat. No. 4,711,896; U.S. Pat. No. 5,756,544; U.S. Pat. No. 6,506,799). Phosphates of dolichol (U.S. Pat. No. 4,613,593), and azolidinedione derivatives (U.S. Pat. No. 4,287,200) can also be used to reduce cholesterol levels. A combination therapy regimen may be additive, or it may produce synergistic results (e.g., reductions in cholesterol greater than expected for the combined use of the two agents). In some embodiments, combination therapy with an antigenic PCSK9 peptide or an immunogenic composition or a pharmaceutical composition thereof and a statin produces synergistic results (e.g., synergistic reductions in cholesterol). In some subjects, this can allow reduction in statin dosage to achieve the desired cholesterol levels.

Another embodiment of the invention relates to the use of a vaccine construct of the invention in the manufacture of a medicament for the treatment of a PCSK9-related disorder or condition, as described above.

Another embodiment of the invention relates to the use of an immunogenic composition of the invention in the preparation of a medicament for the treatment of a PCSK9-related disorder or condition, as described above.

Another embodiment of the invention relates to a vaccine construct of the invention for use in the treatment of a PCSK9-related disorder or condition, as described above. In these embodiments, the vaccine construct may be designed to be administered as a pharmaceutical composition including at least one excipient, as described above.

Other specific embodiments include methods of treating a PCSK9-related disorder or condition, as described above, in an individual comprising administering an effective amount of a vaccine construct of the invention to an individual in need thereof.

Each publication or patent document cited in this disclosure is incorporated herein by reference in its entirety.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

This example describes the conjugation of PCSK9 peptide NVPEEDGTRFHRQASKC (SEQ ID NO:3) to Qbeta bacteriophage VLPs using the bifunctional cross-linker SMPH (Pierce Endogen, Ill.), described previously (Hunter, et al. 2011 Vaccine 29(28):4584-92). As depicted in FIG. 1, this technique links the C-terminal cysteine on the PCSK9 peptide to exposed surface lysine residues on the coat protein of Qbeta. Conjugation efficiency was monitored by SDS-PAGE analysis. Each Qbeta-PCSK9 particle displayed an average of 270 peptides per VLP.

Example 2

Figures 2A, 2B:
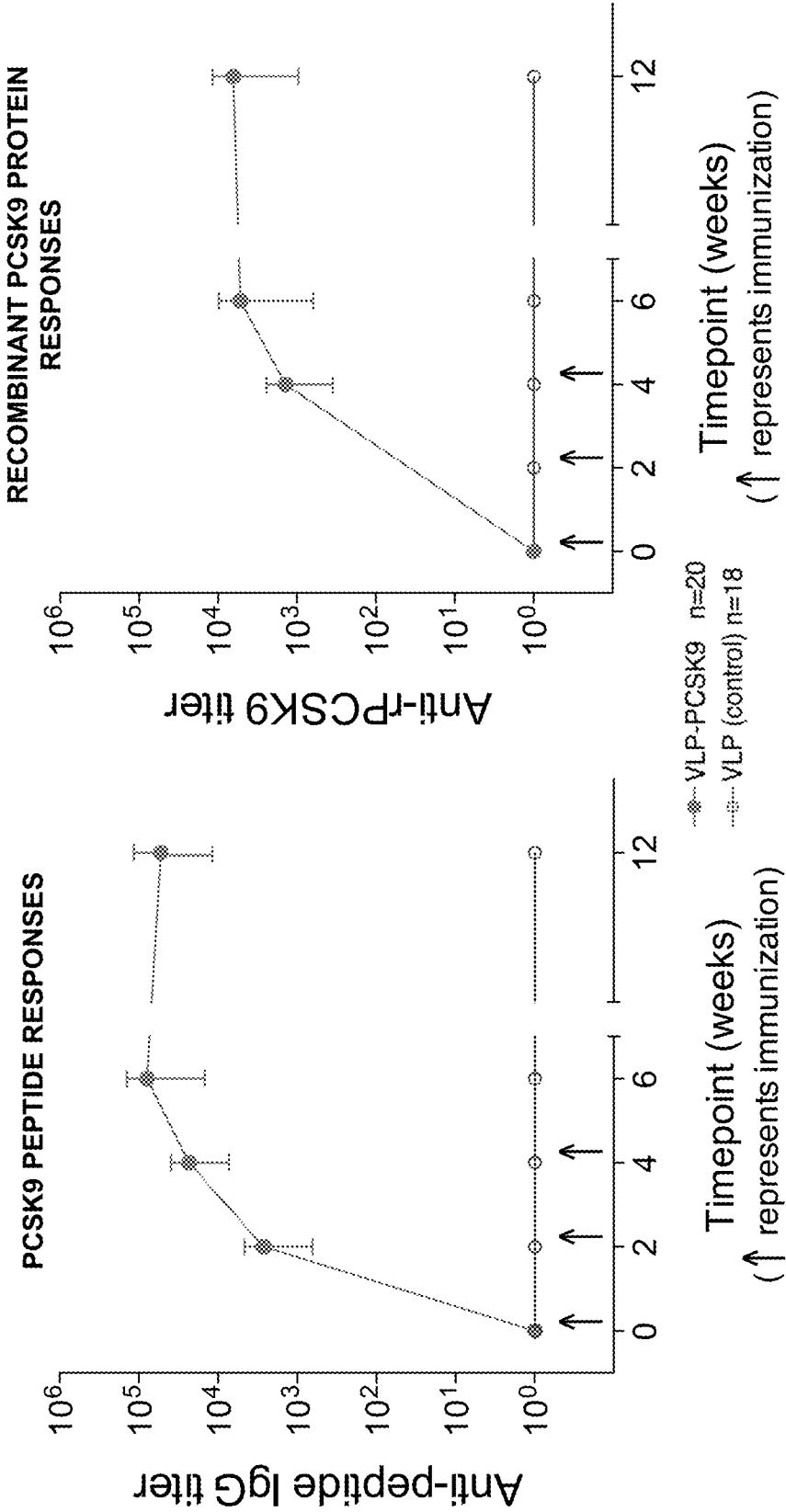
FIGS. 2A and 2B show the mean end-point dilution IgG titers in Balb-c mice immunized with the PCSK9-Qbeta produced by the linking methodology depicted in FIG. 1.

This example describes the mean end-point dilution IgG titers produced in mice immunized with PCSK9-Qbeta formed as described in Example 1, or wild-type Qbeta VLPs (as a control) (FIGS. 2A and 2B). Mice were immunized at weeks 0, 2, and 4 and sera was analyzed prior to each vaccination and at weeks 6 and 12. FIG. 2A shows the end-point dilution titers against a synthetic PCSK9(207-223) peptide (SEQ ID NO:3). FIG. 2B shows end-point dilution titers against full-length human PCSK9 (SEQ ID NO:2). n=20 (PCSK9-Qbeta), 18 (controls). In FIGS. 2A and 2B, error bars show standard deviation (SD). These data demonstrate that vaccination with the PCSK9-Qbeta construct of the invention elicits high titer antibody responses against PCSK9.

Example 3

Figures 3A, 3B:
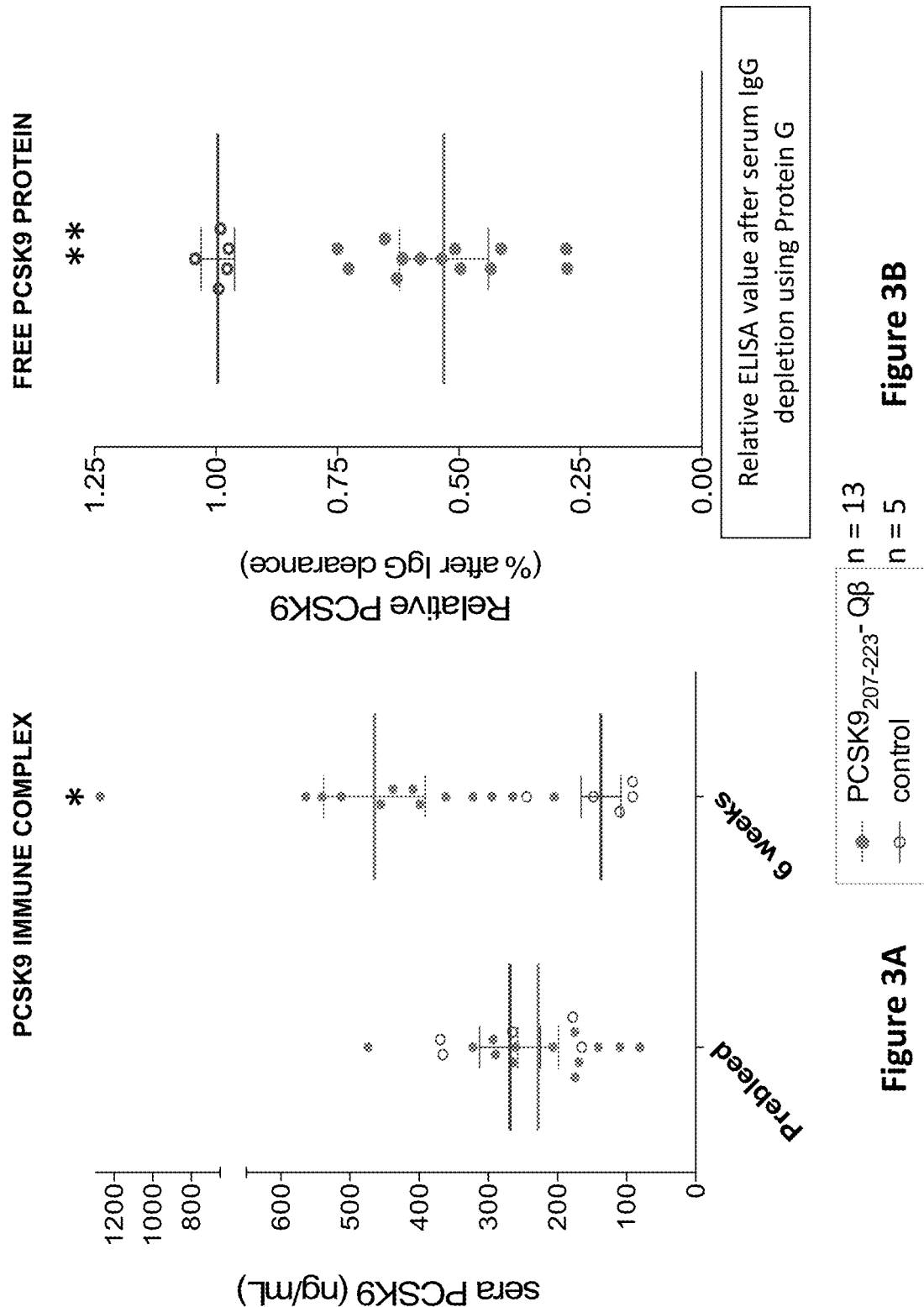
FIGS. 3A and 3B show the serum-associated PCSK9 in PCSK9-Qbeta (grey circle) or control (open circle) vaccinated mice.

This example describes testing of the levels of serum-associated PCSK9 protein in mice vaccinated with the PCSK9-Qbeta of the invention as prepared in Example 1, FIG. 3A and 3B, (grey circle) or control (open circle). FIG. 3A shows the serum taken from mice prior to vaccination (prebleed) or after 3 immunizations and then assessed for PCSK9 protein by ELISA. After vaccination, the PCSK9 levels in PCSK-Qbeta-immunized mice were significantly higher than in controls. FIG. 3B shows the sera reacted with Protein G (to deplete IgG) and then retested by ELISA for PCSK9 protein to assess whether PCSK9 protein was associated with immune complexes. In FIGS. 3A and 3B, each dot represents an individual mouse, lines reflect mean values for each group, and error bars reflect the standard error of the mean, and asterisk (*) indicates $p<0.05$, and (**) indicates $p<0.001$. Protein G depletion did not effect the PCSK9 levels in control vaccinated mice, but resulted in a significant (50%) reduction in PCSK9 protein levels in mice immunized with the PCSK9-Qbeta construct of the invention. These data demonstrate that vaccinated mice had elevated serum PCSK9 protein bound to IgG.

Example 4

Figure 4:
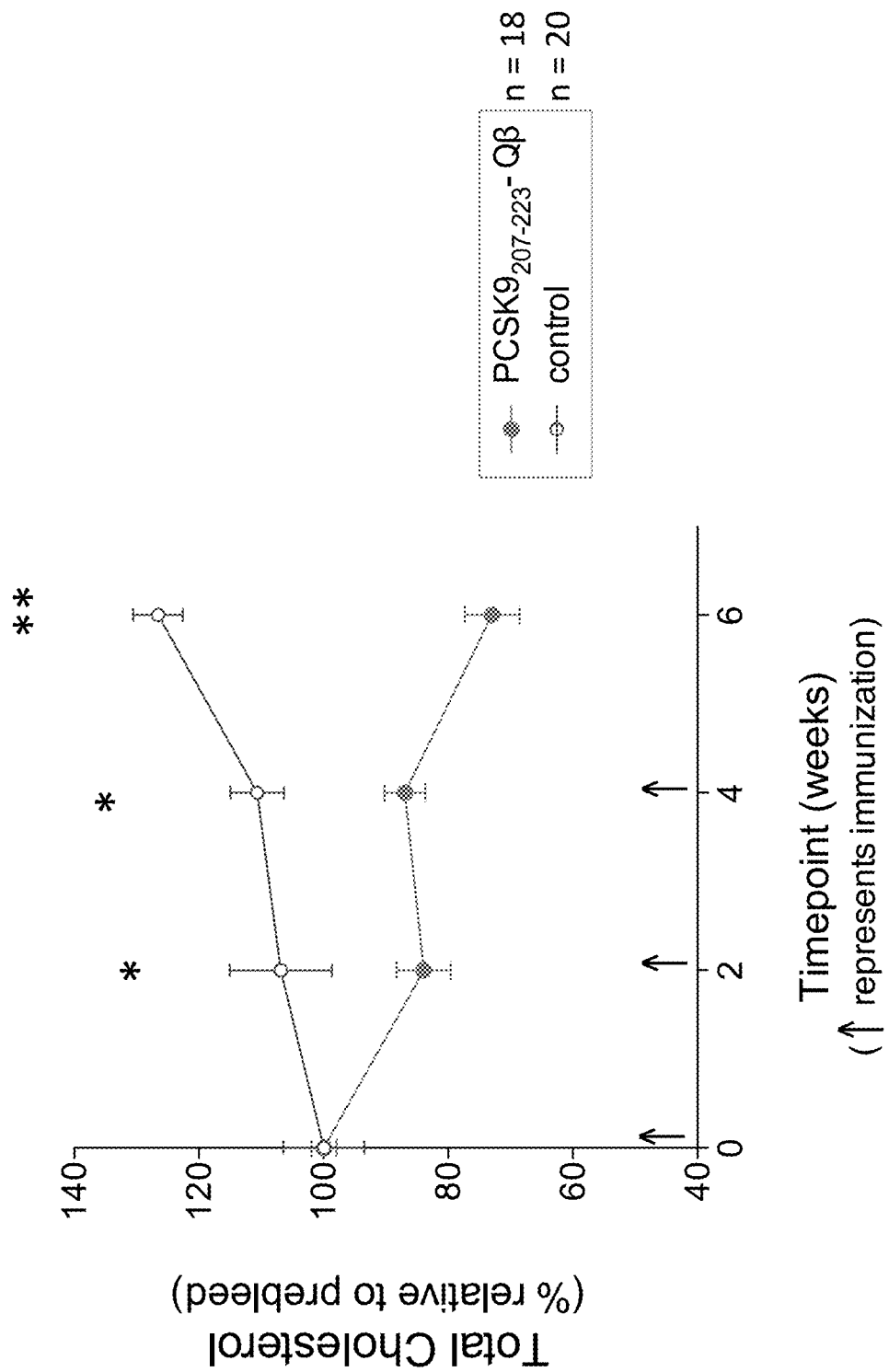
FIG. 4 shows plasma total cholesterol from PCSK9- and control-vaccinated mice.

This example describes the analysis of plasma total cholesterol from mice vaccinated with the PCSK9 vaccine construct as prepared in Example 1, and control vaccinated mice. Balb/C mice were immunized at the indicated time points with either PCSK9-Qbeta (grey circle) or control (open circle) vaccine (FIG. 4). At baseline and 2-weeks after vaccination, plasma was obtained and total cholesterol was enzymatically measured on a ChemWell analyzer. In FIG. 4, each dot reflects mean values for each group, and error bars reflect the standard error of the mean, and asterisk (*) indicates $p<0.05$, and (**) indicates $p<0.001$. As demonstrated in FIG. 4, vaccination resulted in an approximate 50% decrease in total cholesterol in the PCSK9-Qbeta immunized group.

Example 5

Figures 5A, 5B:
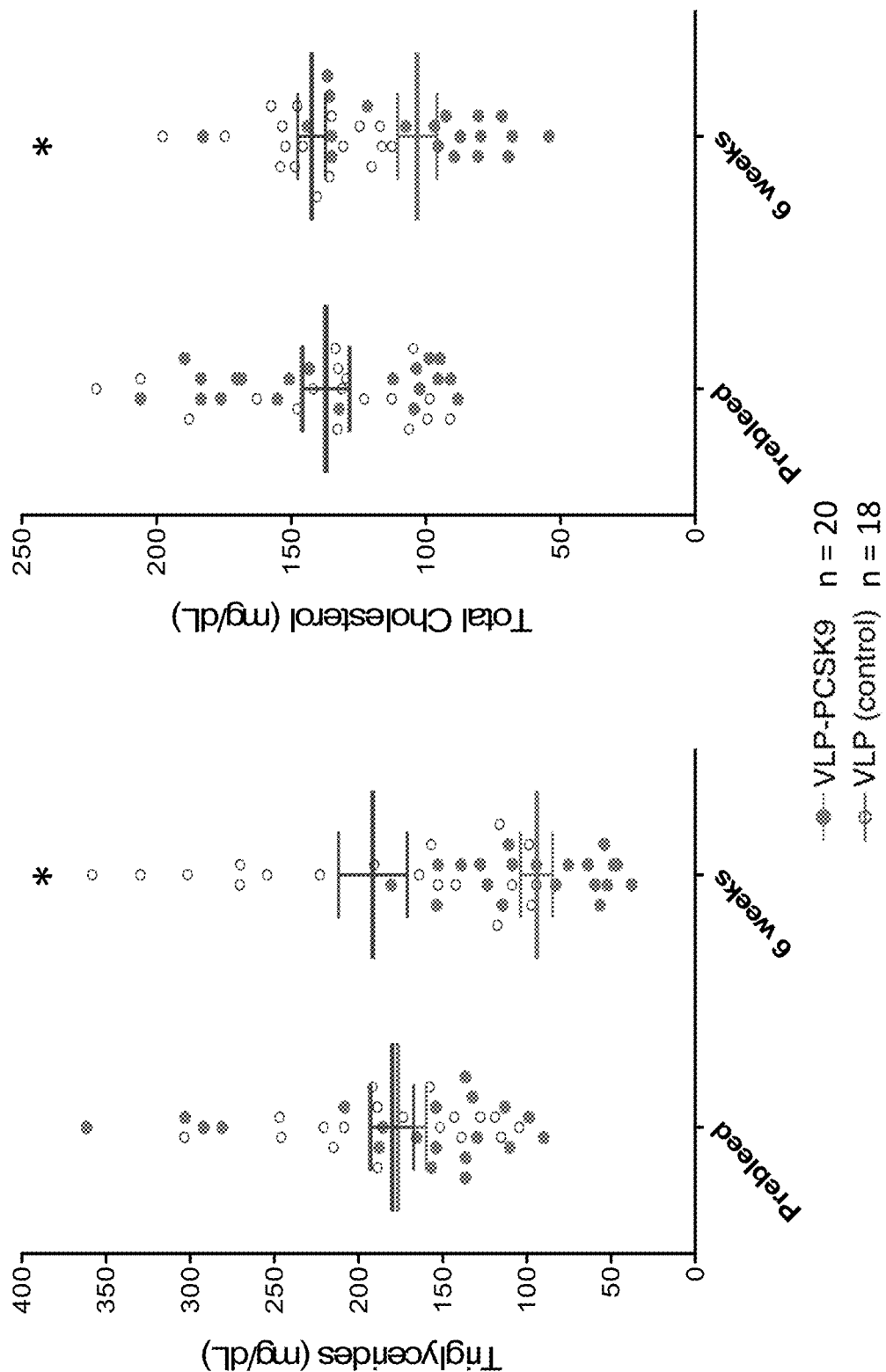
FIGS. 5A and 5B show plasma total triglycerides and cholesterol, respectively, from PCSK9 and control-vaccinated mice.

This example describes the analysis of plasma total triglycerides and cholesterol from mice vaccinated with the PCSK9 vaccine construct as prepared in Example 1, and control vaccinated mice. Balb/C mice were immunized three times at 2-week intervals with either PCSK9-Qbeta (grey circle) or control (open circle) vaccine (FIGS. 5A and 5B). At baseline and 6-weeks after vaccination, plasma was obtained and total triglyceride cholesterol was enzymatically measured on a ChemWell analyzer. In FIGS. 5A and 5B, each dot represents an individual mouse, lines reflect mean values for each group, and error bars reflect the standard error of the mean, and asterisk (*) indicates $p<0.001$. As demonstrated in FIGS. 5A and 5B, lipids (triglycerides and total cholesterol, respectively) were significantly reduced in the PCSK9-Qbeta immunized group.

Example 6

Figures 6A, 6B:
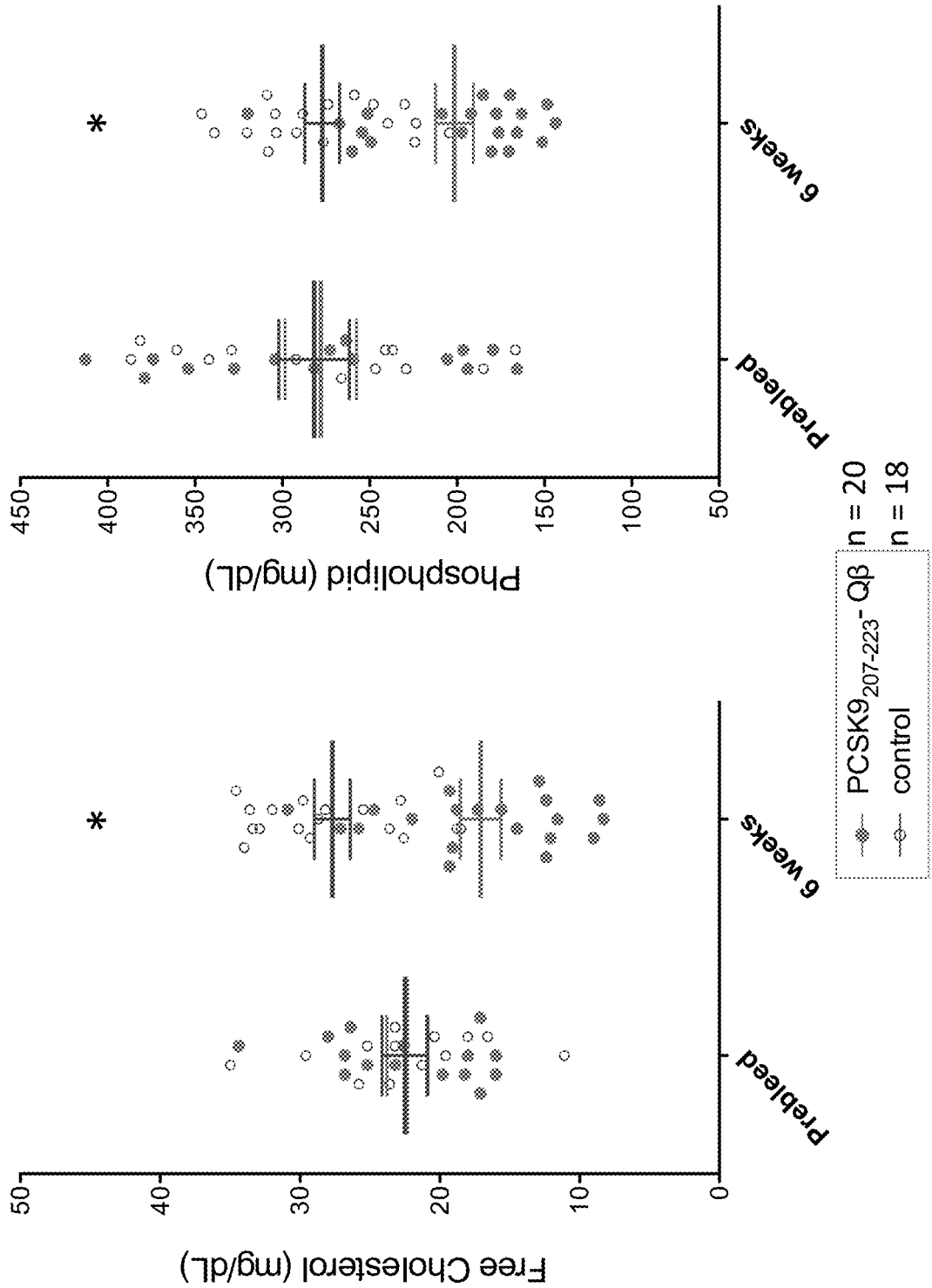
FIGS. 6A and 6B show plasma free cholesterol and phospholipid, respectively, from PCSK9- and control-vaccinated mice.

This example describes the analysis of plasma free cholesterol and phospholipid from PCSK9-Qbeta and control vaccinated mice. Balb/C mice were immunized three times at 2-week intervals with either PCSK9-Qbeta (grey circle) or control (open circle) vaccine (FIGS. 6A and 6B). At baseline and 6-weeks after vaccination, plasma was obtained and free cholesterol (FIG. 6A) and phospholipid (FIG. 6B) was enzymatically measured on a ChemWell analyzer. In FIGS. 6A and 6B, each dot represents an individual mouse, lines reflect mean values for each group, and error bars reflect the standard error of the mean, and asterisk (*) indicates $p<0.001$. As demonstrated in FIGS. 6A and 6B, lipids (free cholesterol and phospholipids, respectively) were significantly reduced in the PCSK9-Qbeta immunized group.

Example 7

Figure 7A:
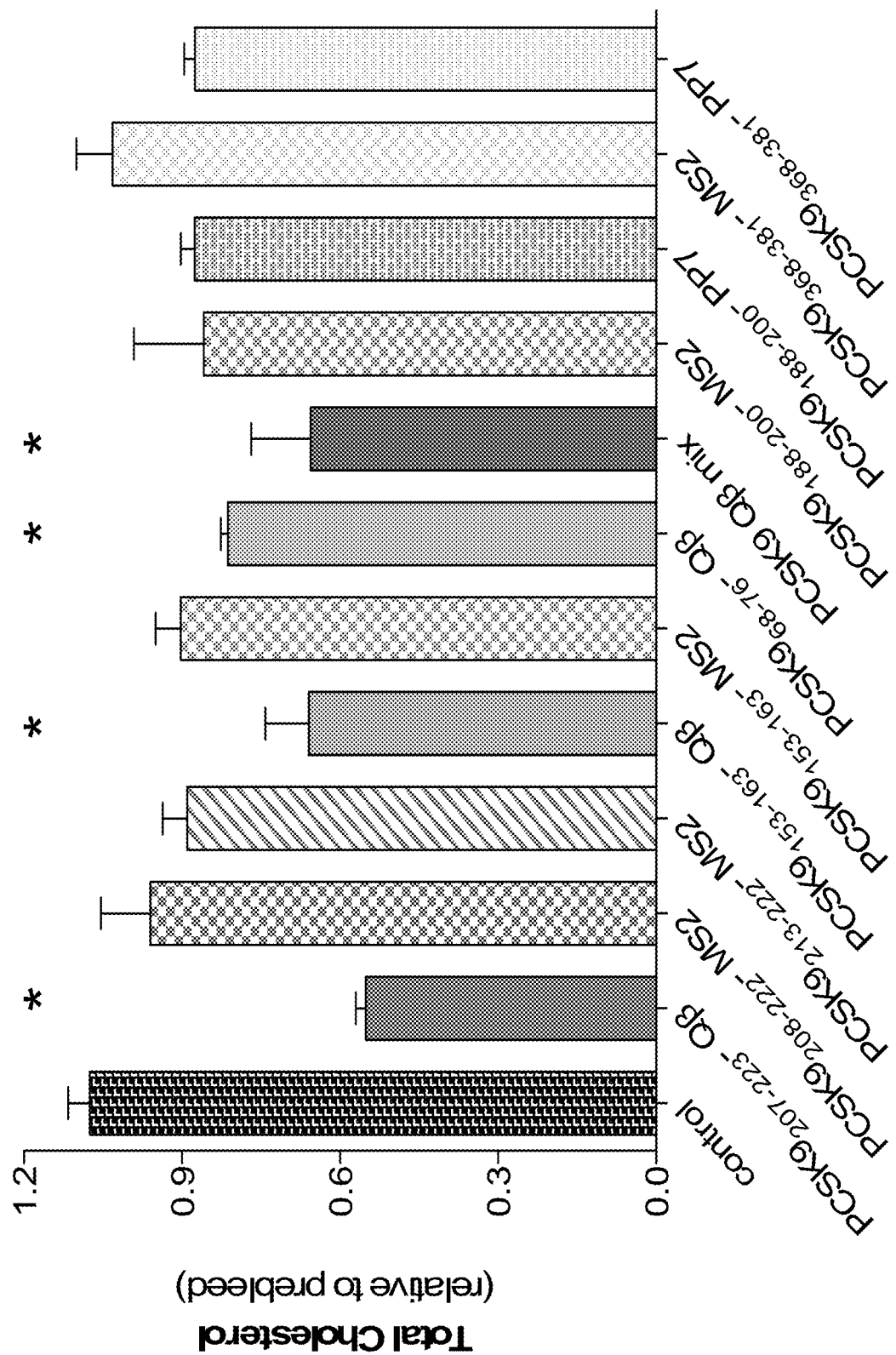
FIGS. 7A, 7B, 7C, and 7D show lipid changes in male mice immunized with PCSK9 peptides attached to different VLP particles.
Figure 7B:
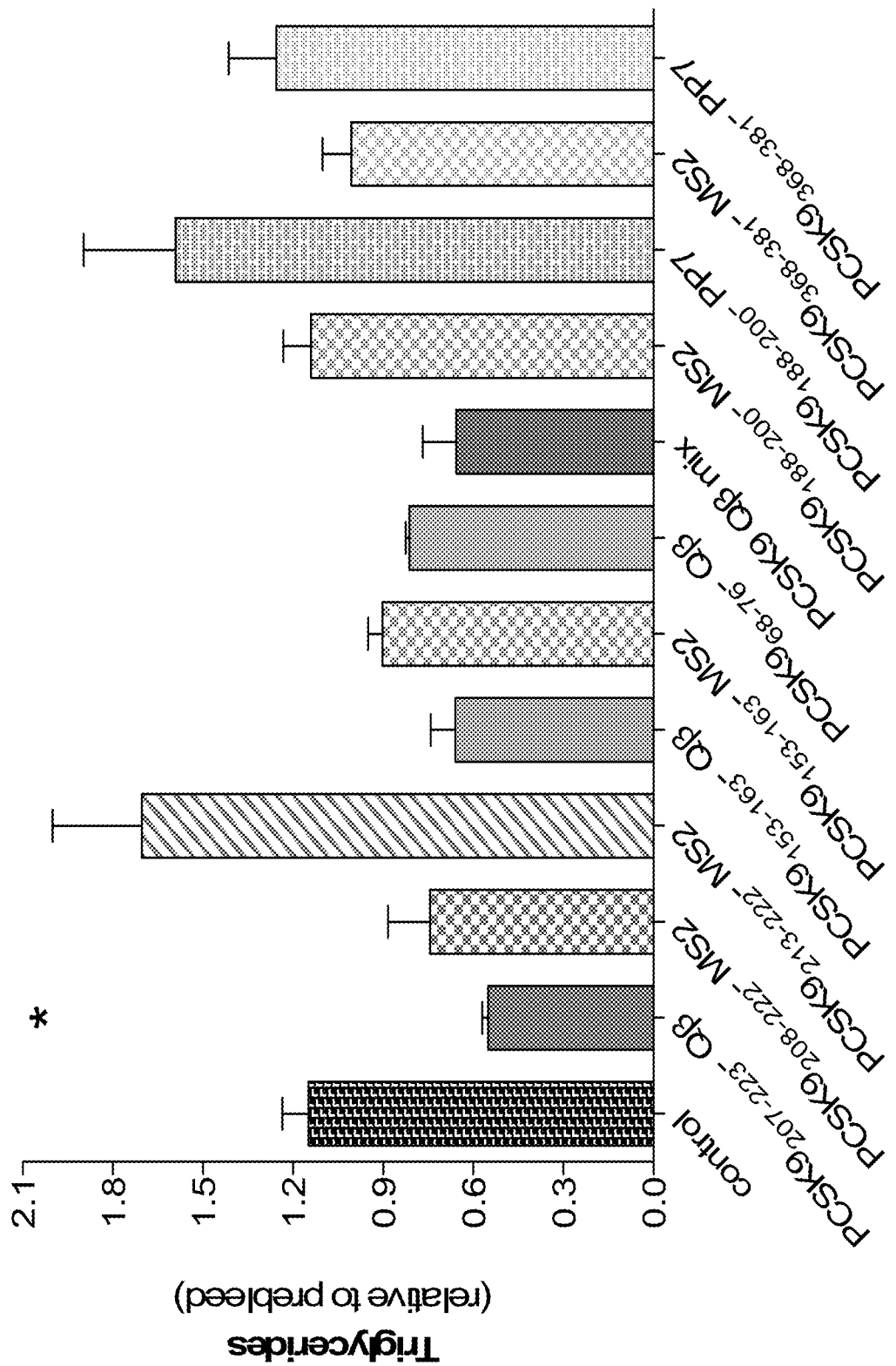
Figure 7C:
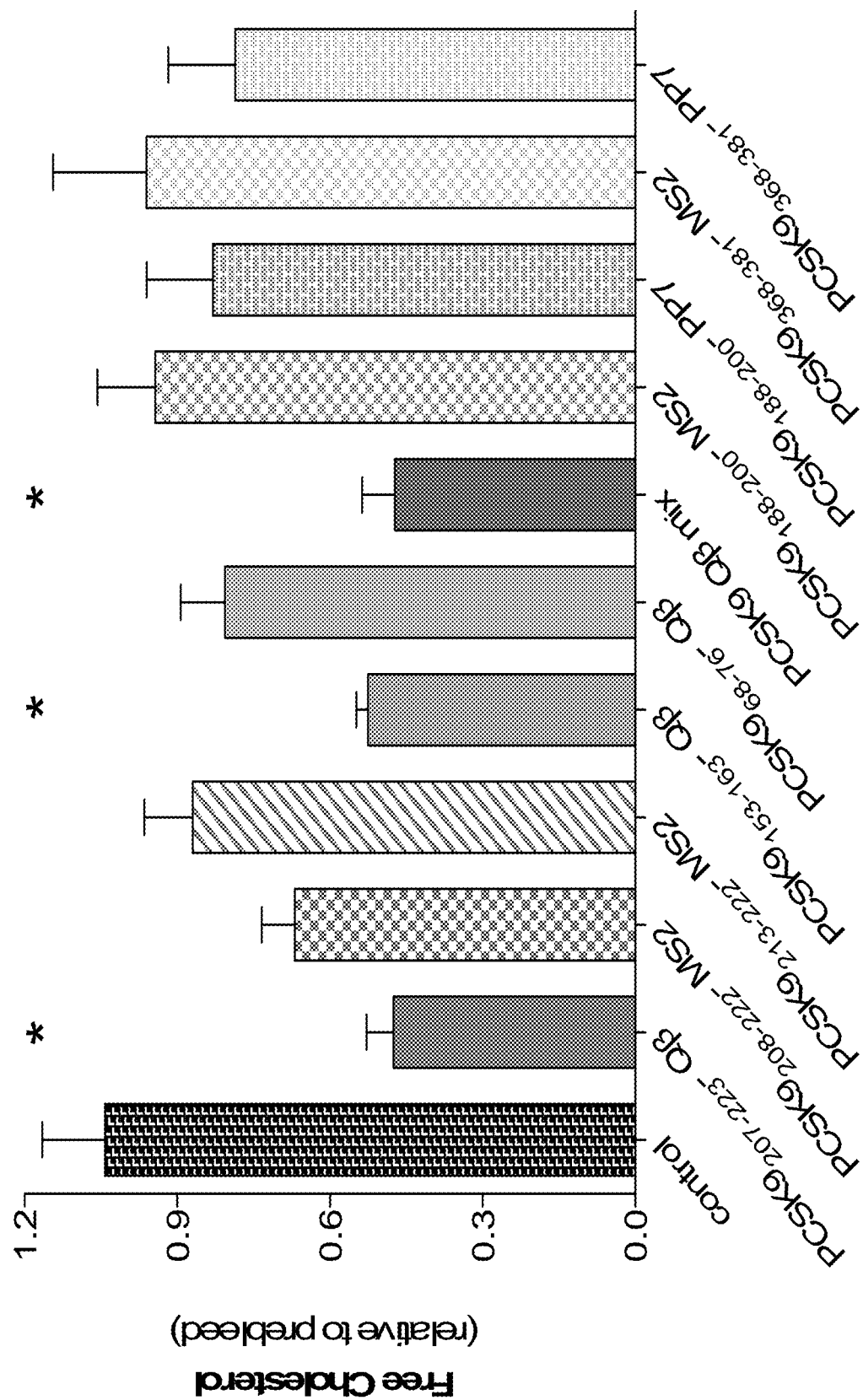
Figure 7D:
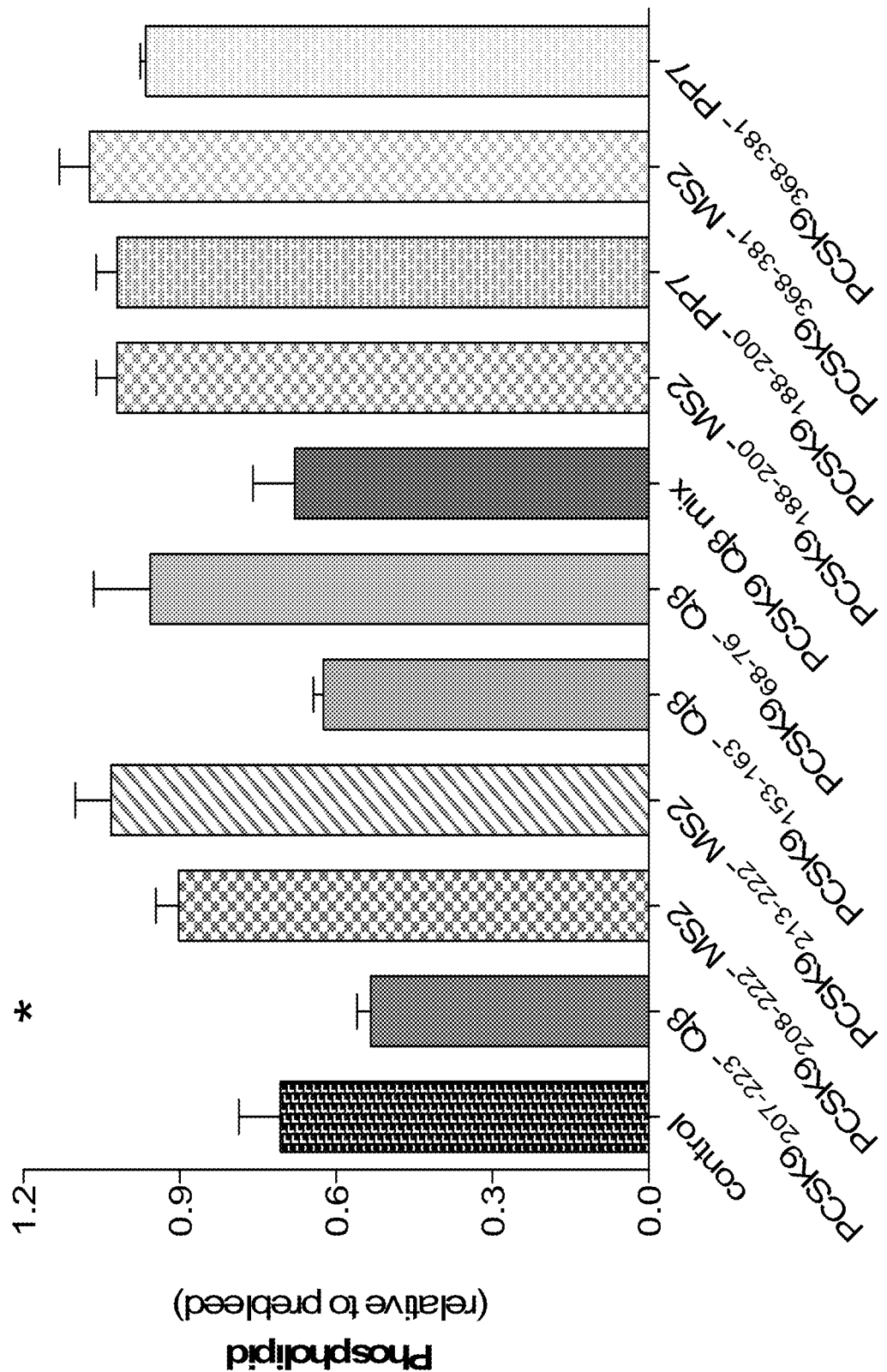
Figure 7E:
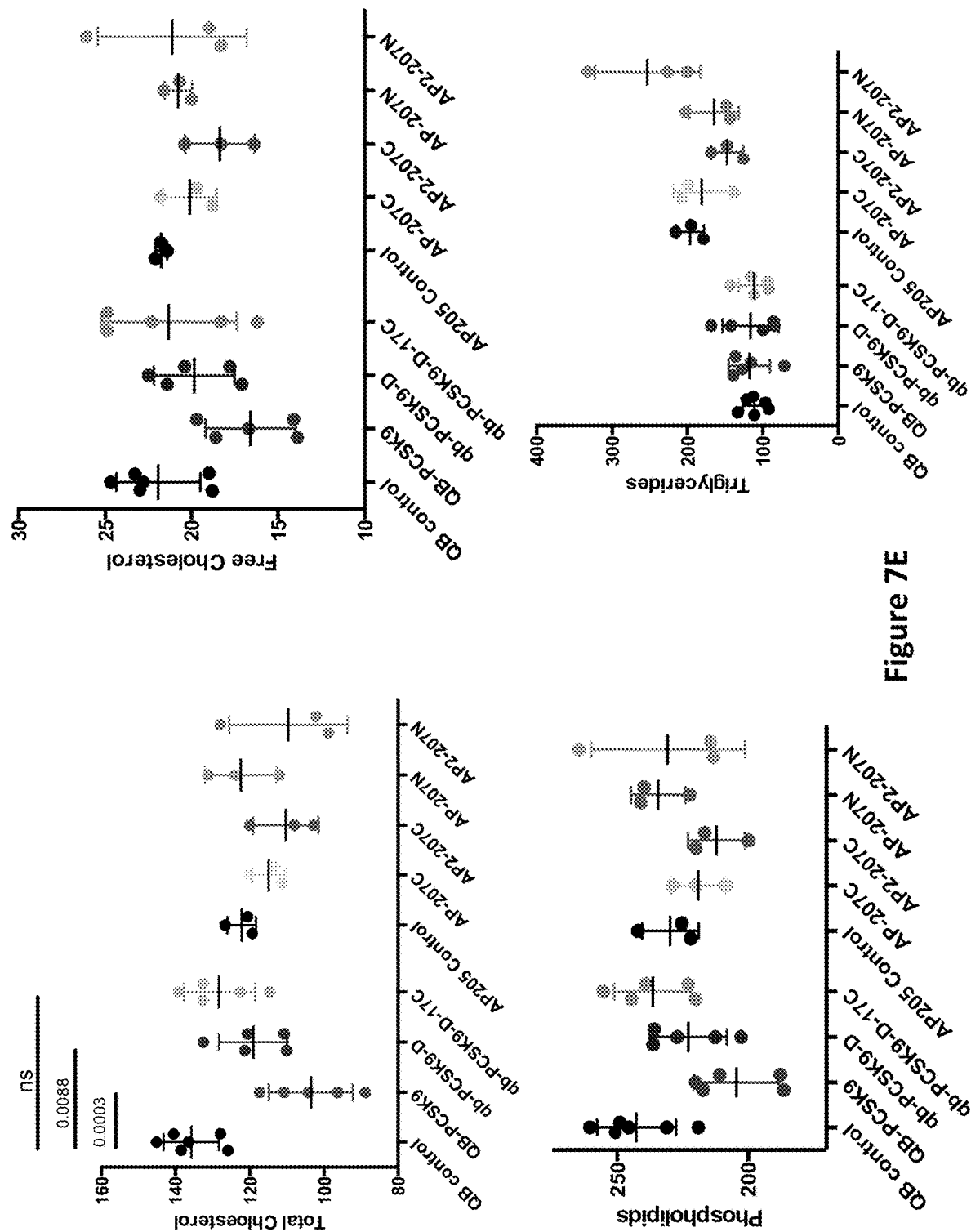
FIG. 7E shows a comparison of lipid data from mice immunized with the Qβ VLP-PSCK9(207-223) construct, and the same VLPs displaying the retroinverso peptides (PCSK9-D and PCSK9-D-17C).

This example describes the analysis of lipid changes in male Balb/C mice, immunized with several PCSK9 peptides attached to several different VLP particles. The VLP particles included Qβ, MS2, and PP7. The PCSK9 peptides included amino acids 207-223, 208-222, 213-222, 153-163, 68-76, 188-200, and 368-381 (amino acid positions are relative to the mouse PCSK9 (SEQ ID NO:1)). The peptides were chemically conjugated to the Qβ VLP. The MS2 and PP7 VLPs are recombinant particles. The effect of each construct on total cholesterol (FIG. 7A), Triglycerides (FIG. 7B), Free Cholesterol (FIG. 7C) and Phospholipids (FIG. 7D) are shown (data shown is relative to prebleed values). FIG. 7E shows a comparison of lipid data from mice immunized with the Qβ VLP-PSCK9(207-223) construct, the Qβ VLPs displaying the retroinverso peptides (labeled PCSK9-D and PCSK9-D-17C) and four different recombinant AP205 VLPs displaying the PCSK9(207-223) peptide at either the N- or C-terminus of the viral coat protein. For each of FIGS. 7A-7E, values are expressed as Mean/SEM, and asterisk (*) indicates $p<0.05$. These data indicate a greater efficacy for constructs based on the Qβ VLP and additionally show that even single amino shifts in the chosen PCSK9 peptide impart significant differences to the therapeutic effect of the construct following immunization.

Figure 12:
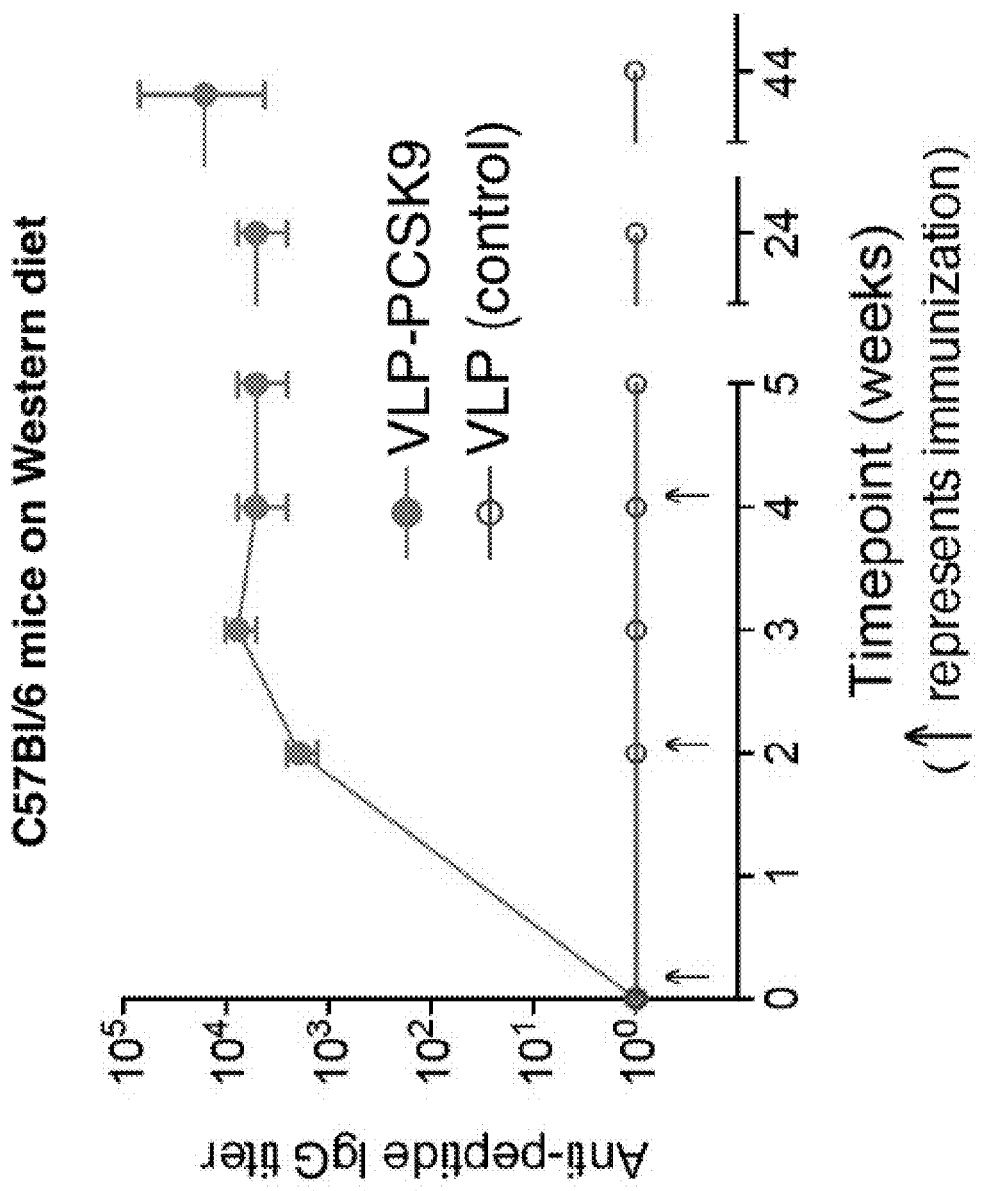
FIG. 12 shows that immunized mice maintained on a high-fat Western diet developed high-titer anti-peptide IgG responses that cross-reacted with PCSK9, which remained stable and persisted for at least 44 weeks after first immunization.

The immunized C57B1/6 mice were maintained on Western diet (n=3 per group) and followed beyond 44 weeks. FIG. 12 shows that the immunized mice developed high-titer anti-peptide IgG responses that cross-reacted with PCSK9, which remained stable and persisted for at least 44 weeks after first immunization.

Example 8

Figure 8:
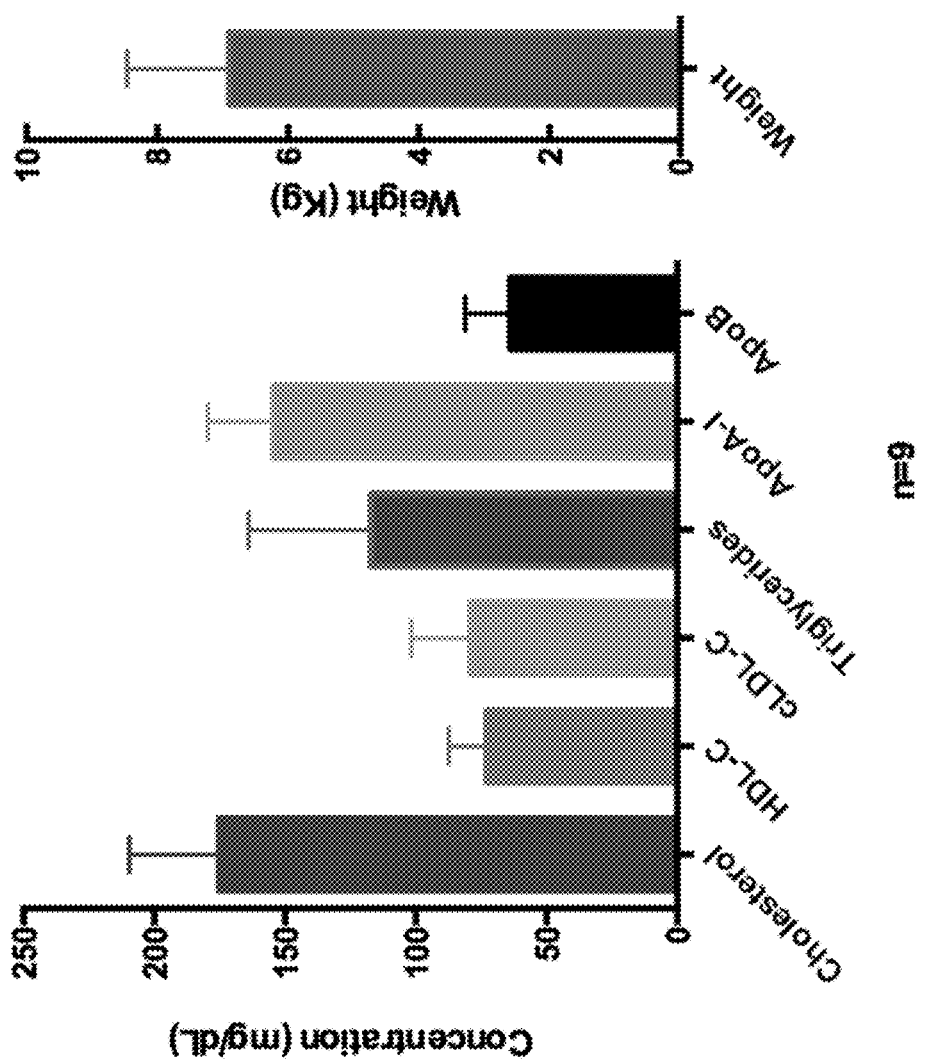
FIG. 8 provides the baseline parameters of lipids in Rhesus monkeys prior to immunization.
Figure 9:
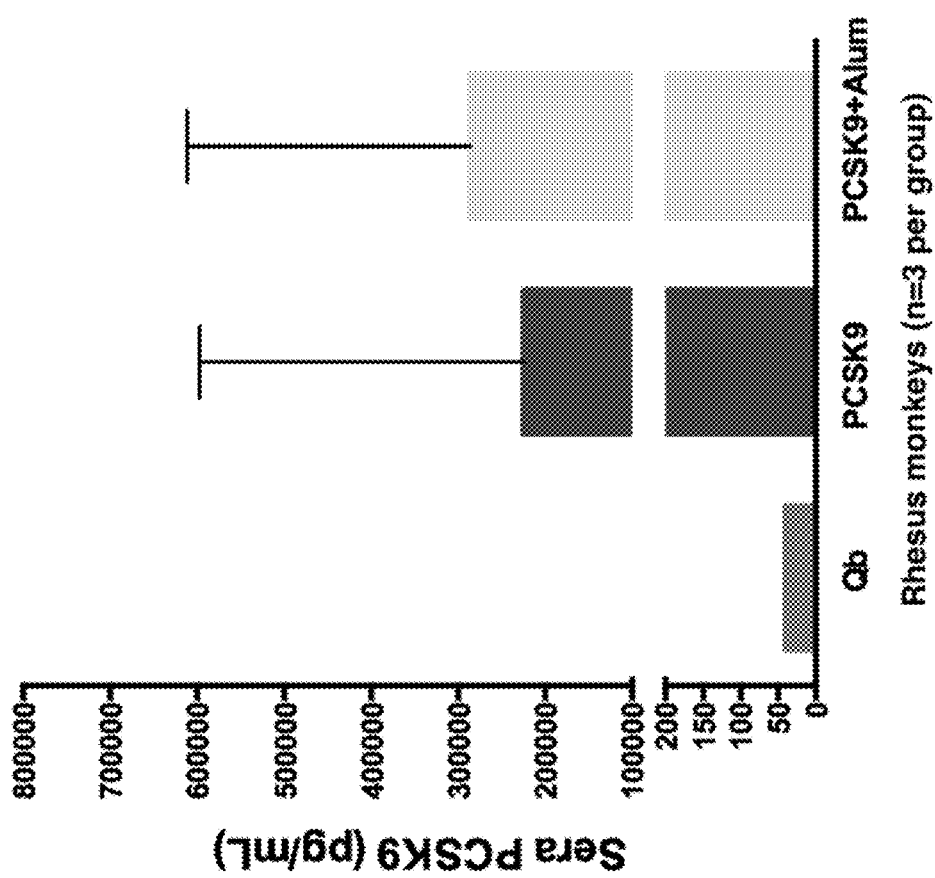
FIG. 9 shows the sera anti-PCSK9 peptide IgG responses that cross-reacted with PCSK9 protein from three groups of monkeys.
Figure 10:
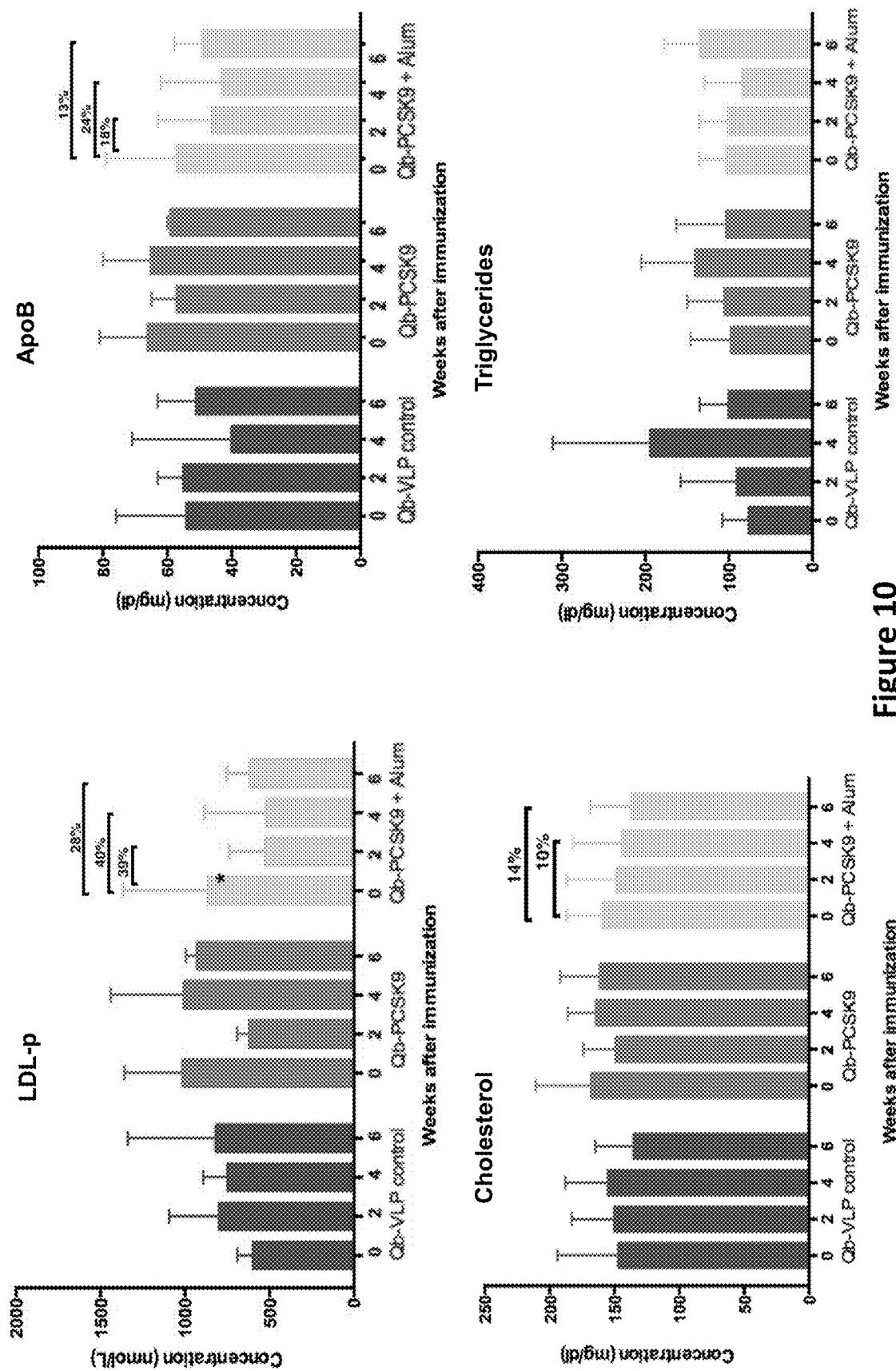
FIG. 10 shows the effect on plasma lipids in immunized monkeys.
Figure 11:
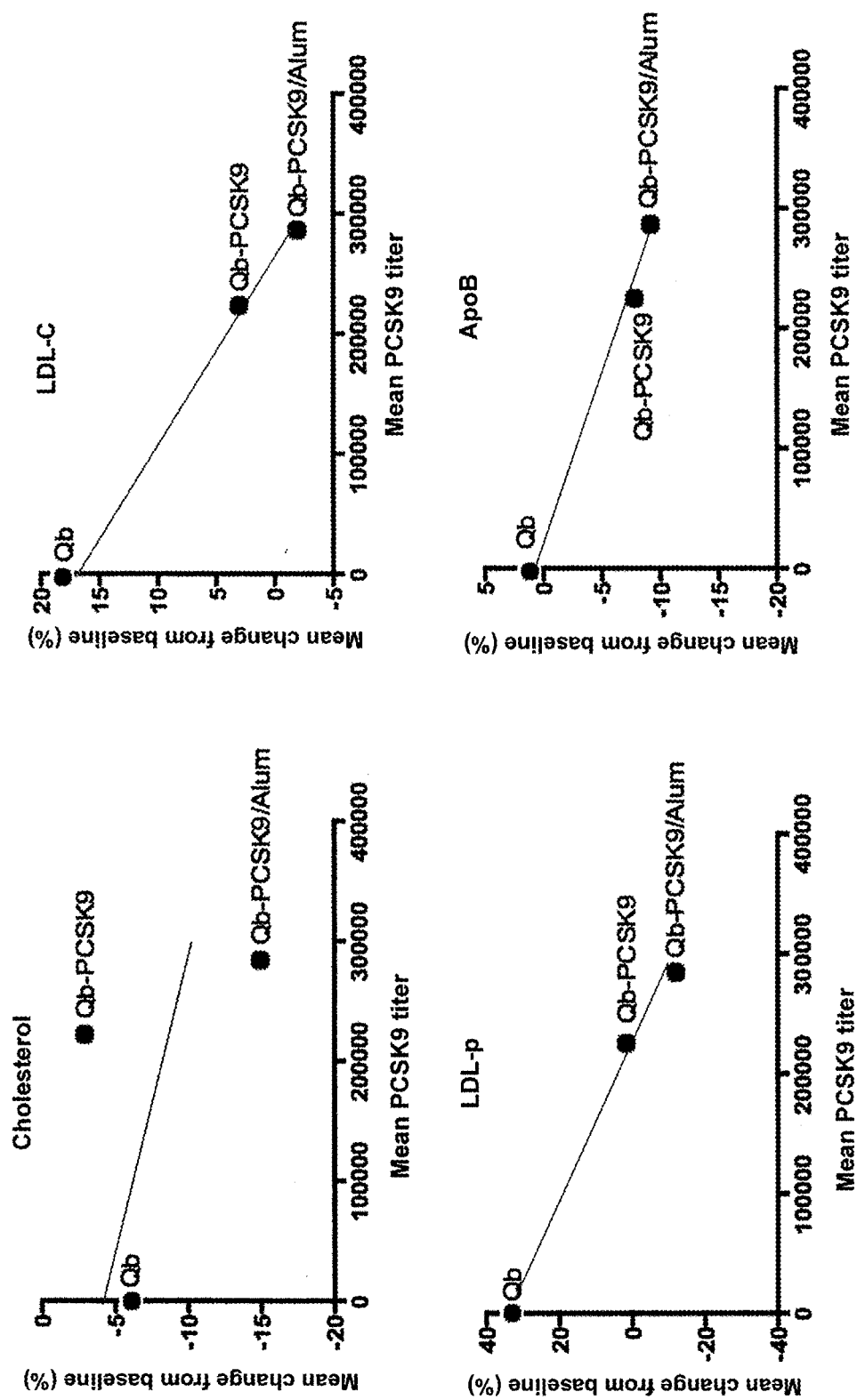
FIG. 11 shows that the plasma lipid changes in the monkeys correlated with titer.
Figure 13:
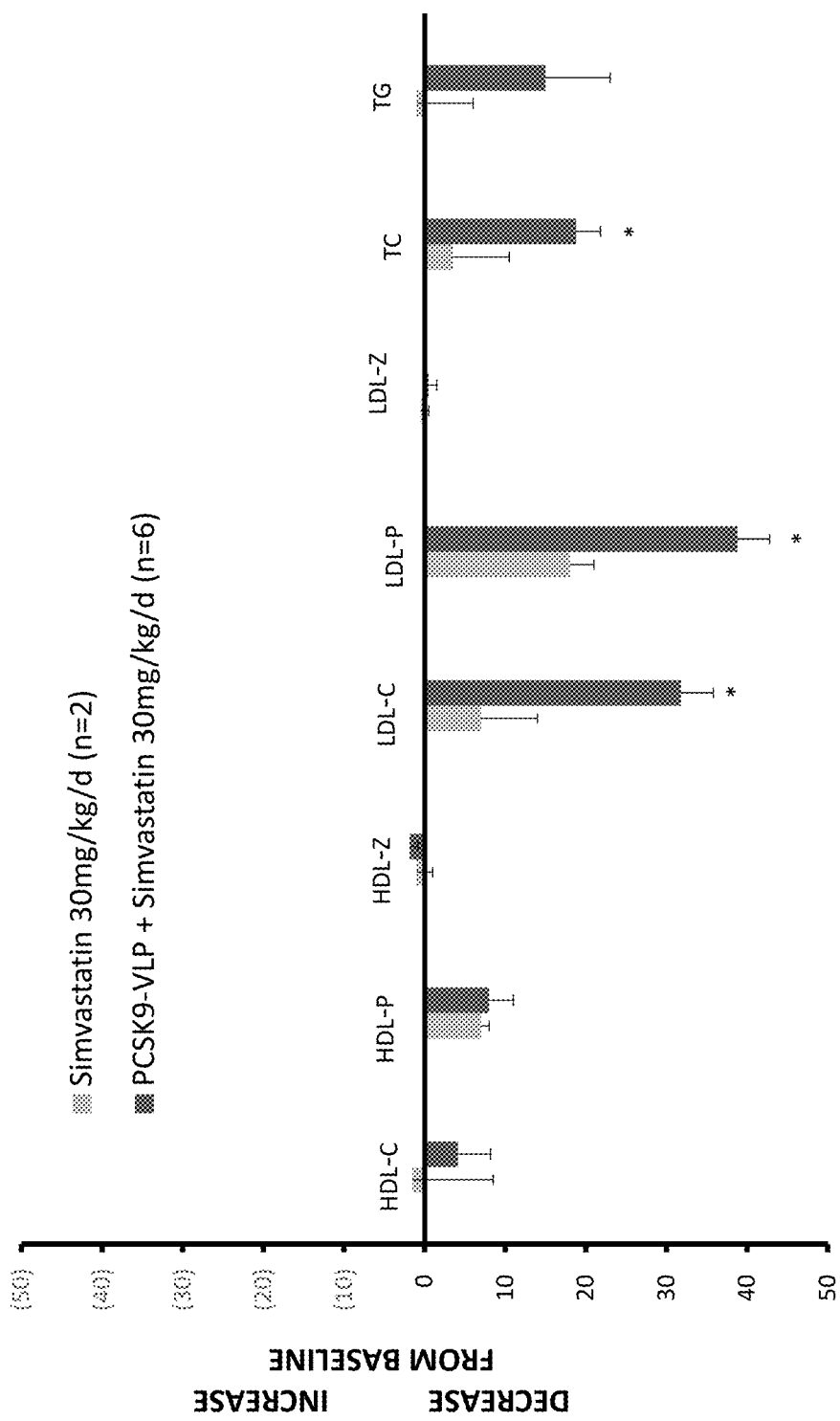
FIG. 13. Monkeys treated with simvastatin 30 mg/kg/d and immunized with Qβ VLP-PSCK9(207-223) showed a synergistic decrease in serum lipids greater than the decrease in serum lipids observed with administration of the statin alone.

Immunogenicity of PCSK9-Qβ was determined by immunizing male Rhesus monkeys intramuscularly three times at 2-week intervals with 50 μg of column-purified (1) wild-type (control) or (2) PCSK9-conjugated VLPs, or (3) PCSK9-conjugated VLPs with alum adjuvant (1:4). Plasma collection from each monkey was collected at baseline, day 0, day 14, day 28 and day 42. At each time point, plasma lipid parameters were collected and at the end of the study, an IgG titer and a plasma PCSK9 quantification was determined. FIG. 8 shows the mean and SEM plasma lipid parameters from the monkeys at baseline. The PCSK9-VLP vaccine was well tolerated with no signs of overt toxicity in both species. FIG. 9 shows the sera PCSK9 for groups (1)-(3) of the monkeys, demonstrating that immunized NHP (n=3 per group) developed high-titer anti-peptide IgG responses that cross-reacted with PCSK9 protein. FIG. 10 shows the effect on plasma lipids in groups (1)-(3) of the monkeys. Vaccination resulted in changes in lipoprotein profile at week 2: Decreases in TC (−14.2%), ApoB (−13.4%) and LDL-p (−28.4%) were observed after 6 weeks. FIG. 11 shows that the plasma lipid changes correlated with the titer in the monkeys. FIG. 13 shows that monkeys treated with simvastatin 30 mg/kg/d, addition of immunization with Qβ VLP-PSCK9(207-223) construct showed a synergistic therapeutic decrease in serum lipids well beyond the administration of the statin alone.

Collectively, the data in these Examples demonstrate that the inventors have developed a new strategy to reduce LDL-C based on immunization against PCSK9. The preliminary studies showed high titers of PCSK9 antibody with no toxicity, and initial mouse and non-human primate studies showed response to immunization by producing anti-PCSK9 antibodies and reduction of LDL-p (40%), ApoB (24%) and TC (15%), which may translate in approximately 50% protection over the lifetime of a patient. Thus, immunization against PCSK9 is a promising new approach to different forms of hypercholesterolemia, as well as acute coronary syndrome.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A composition comprising:
   a first antigenic proprotein convertase subtilisin-kexin type 9 (PCSK9) peptide linked to a bacteriophage virus-like particle (VLP) Qbeta immunogenic carrier, the first antigenic PCSK9 antigenic peptide comprising the amino acid sequence NVPEEDGTRFHRQASKC (SEQ ID NO:3); and
   a second antigenic PCSK9 linked to a VLP Qbeta immunogenic carrier, the second antigenic PCSK9 peptide comprising:
   the amino acid sequence SIPWNLERIIP (amino acids 150-160 of SEQ ID NO:1), or
   the amino acid sequence SIPWNLERITP (amino acids 153-163 of SEQ ID NO:2).

2. The composition of claim 1, wherein at least one amino acid is in the D-isomeric form.

3. The composition of claim 1, wherein at least one immunogenic carrier is linked to the first PCSK9 peptide or the second PCSK9 peptide through a succinimidyl-6[β-maleimidopropionamido]hexanoate (SMPH) cross-linker molecule.

4. The composition of claim 1, wherein the first PCSK9 antigenic peptide and the second PCSK9 antigenic peptide are linked to the same VLP Qbeta immunogenic carrier.

5. The composition of claim 1, wherein:
   at least one first antigenic PCSK9 peptide is linked to a first VLP Qbeta immunogenic carrier; and
   at least one second antigenic PCSK peptide is linked to a second VLP Qbeta immunogenic carrier.

6. The composition of claim 1, further comprising at least one adjuvant.

7. A method of preventing, alleviating, or treating a dyslipidemia in an individual, the method comprising administering a therapeutically effective amount of the composition of claim 1 to the individual.

8. The method according to claim 7, wherein the dyslipidemia is selected from a group of hyperlipidemias consisting of type I, type II, type III, type IV, or type V hyperlipidemia, secondary hypertriglyceridemia, secondary hypercholesterolemia, hypercholesterolemia, familial hypercholesterolemia, familial combined hyperlipidemia xanthomatosis, and lecithin:cholesterol acetyltransferase deficiency.

9. The method of claim 7, wherein the composition is administered in combination with at least one additional therapeutic agent selected from the group consisting of a statin, a bile acid sequestrant, niacin, a fibric acid derivative, and a long chain alpha, omego-dicarboxylic acid.

10. A method of preventing, alleviating, or treating a condition selected from atherosclerosis, coronary artery disease, cardiovascular disease, and acute coronary syndrome in an individual, the method comprising administering a therapeutically effective amount of the composition of claim 1 to the individual.

11. The method of claim 10, wherein the composition is administered in combination with at least one additional therapeutic agent selected from the group consisting of a statin, a bile acid sequestrant, niacin, a fibric acid derivative, and a long chain alpha, omego-dicarboxylic acid.

12. A method of preventing, alleviating, or treating hypertriglyceridemia in an individual, the method comprising administering a therapeutically effective amount of the composition of claim 1 to the individual.

13. The method of claim 12, wherein the composition is administered to the individual in combination with at least one adjuvant.

14. The method of claim 12, wherein the composition is administered to the individual in combination with at least one of a statin and a fabric acid derivative.

* * * * *

UNITED STATES PATENT AND TRADEMARK OFFICE
CERTIFICATE OF CORRECTION

PATENT NO. : 10,925,938 B2
APPLICATION NO. : 16/250514
DATED : February 23, 2021
INVENTOR(S) : Remaley et al.

Page 1 of 1

It is certified that error appears in the above-identified patent and that said Letters Patent is hereby corrected as shown below:

In the Claims

In Column 44, Line 34, 'fabric' should read -fibric-

In Column 44, Line 46, 'fabric' should read -fibric-

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*